(12) United States Patent
Krummen et al.

(10) Patent No.: US 11,189,092 B2
(45) Date of Patent: Nov. 30, 2021

(54) COMPUTATIONAL LOCALIZATION OF FIBRILLATION SOURCES

(71) Applicant: The Regents of the University of California, Oakland, CA (US)

(72) Inventors: David Krummen, Del Mar, CA (US); Andrew D. McCulloch, San Diego, CA (US); Christopher T. Villongco, San Diego, CA (US); Gordon Ho, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/444,340

(22) Filed: Jun. 18, 2019

(65) Prior Publication Data

US 2019/0304183 A1 Oct. 3, 2019

Related U.S. Application Data

(63) Continuation of application No. 16/295,934, filed on Mar. 7, 2019, which is a continuation of application
(Continued)

(51) Int. Cl.
*A61B 5/00* (2006.01)
*A61B 5/341* (2021.01)
(Continued)

(52) U.S. Cl.
CPC .............. *G06T 17/20* (2013.01); *A61B 5/341* (2021.01); *A61B 5/361* (2021.01); *A61B 5/6823* (2013.01);
(Continued)

(58) Field of Classification Search
CPC ................ A61B 2576/023; G06T 2207/30048
See application file for complete search history.

(56) References Cited

U.S. PATENT DOCUMENTS 5,273,038 A 12/1993 Beavin
6,501,979 B1 12/2002 Manning et al.
(Continued)

FOREIGN PATENT DOCUMENTS

WO WO-2004102482 A1 11/2004
WO WO-2005072607 8/2005
(Continued)

OTHER PUBLICATIONS

Carrault, Guy, et al. "Temporal abstraction and inductive logic programming for arrhythmia recognition from electrocardiograms." Artificial intelligence in medicine 28.3 (2003): 231-263. (Year: 2003).*
(Continued)

*Primary Examiner* — Santiago Garcia
(74) *Attorney, Agent, or Firm* — Mintz Levin Cohn Ferris Glovsky and Popeo, P.C.

(57) ABSTRACT

A system for computational localization of fibrillation sources is provided. In some implementations, the system performs operations comprising generating a representation of electrical activation of a patient's heart and comparing, based on correlation, the generated representation against one or more stored representations of hearts to identify at least one matched representation of a heart. The operations can further comprise generating, based on the at least one matched representation, a computational model for the patient's heart, wherein the computational model includes an illustration of one or more fibrillation sources in the patient's heart. Additionally, the operations can comprise displaying, via a user interface, at least a portion of the computational model. Related systems, methods, and articles of manufacture are also described.

29 Claims, 12 Drawing Sheets
(8 of 12 Drawing Sheet(s) Filed in Color)

Related U.S. Application Data

No. 15/389,245, filed on Dec. 22, 2016, now Pat. No. 10,319,144.

(60) Provisional application No. 62/271,113, filed on Dec. 22, 2015.

(51) Int. Cl.
*A61B 5/361* (2021.01)
*G06T 5/20* (2006.01)
*G06T 7/00* (2017.01)
*G06T 17/20* (2006.01)

(52) U.S. Cl.
CPC .......... *A61B 5/7246* (2013.01); *A61B 5/7278* (2013.01); *A61B 5/7445* (2013.01); *G06T 5/20* (2013.01); *G06T 7/0012* (2013.01); *G06T 2207/10081* (2013.01); *G06T 2207/10088* (2013.01); *G06T 2207/10116* (2013.01); *G06T 2207/10121* (2013.01); *G06T 2207/30048* (2013.01)

(56) References Cited

U.S. PATENT DOCUMENTS

| | | | |
|---|---|---|---|
| 7,010,347 B2 | 3/2006 | Schecter | |
| 7,286,871 B2 | 10/2007 | Cohen | |
| 7,528,338 B2 | 5/2009 | Ataka | |
| 8,521,266 B2* | 8/2013 | Narayan | A61B 5/04011 600/515 |
| 9,211,110 B2 | 12/2015 | Rubin et al. | |
| 9,706,935 B2* | 7/2017 | Spector | A61B 5/04014 |
| 10,315,144 B2 | 6/2019 | Reichter et al. | |
| 10,556,113 B2 | 2/2020 | Villongco et al. | |
| 10,713,791 B2 | 7/2020 | Krummen et al. | |
| 10,856,816 B2 | 12/2020 | Villongco | |
| 2002/0035334 A1 | 1/2002 | Ooishi et al. | |
| 2004/0015081 A1 | 1/2004 | Kramer et al. | |
| 2004/0176697 A1* | 9/2004 | Kappenberger | A61B 5/0456 600/518 |
| 2007/0016108 A1 | 1/2007 | Bewlay et al. | |
| 2007/0032733 A1* | 2/2007 | Burton | A61B 5/4812 600/509 |
| 2007/0259031 A1 | 2/2007 | Kong et al. | |
| 2007/0270703 A1 | 2/2007 | Szeto et al. | |
| 2008/0021336 A1 | 1/2008 | Dobak | |
| 2009/0306732 A1 | 1/2009 | Chakra et al. | |
| 2010/0016917 A1 | 1/2010 | Efimov et al. | |
| 2010/0152796 A1 | 6/2010 | Schecter | |
| 2010/0280355 A1 | 11/2010 | Grimm et al. | |
| 2010/0298904 A1 | 11/2010 | Blomqvist et al. | |
| 2011/0251504 A1 | 10/2011 | Tereshchenko et al. | |
| 2011/0251505 A1* | 10/2011 | Narayan | A61B 5/0432 600/515 |
| 2011/0307231 A1* | 12/2011 | Kirchner | G06F 19/00 703/11 |
| 2011/0311116 A1 | 12/2011 | Benn | |
| 2012/0035459 A1 | 2/2012 | Revishvili et al. | |
| 2012/0087563 A1* | 4/2012 | Ionasec | G06T 17/00 382/131 |
| 2012/0165674 A1 | 6/2012 | Abe et al. | |
| 2012/0283587 A1 | 11/2012 | Gosh et al. | |
| 2013/0006131 A1* | 1/2013 | Narayan | A61B 5/4839 600/508 |
| 2013/0034203 A1 | 2/2013 | Wang et al. | |
| 2013/0096394 A1* | 4/2013 | Gupta | A61B 5/4848 600/301 |
| 2013/0131529 A1* | 5/2013 | Jia | A61B 5/042 600/510 |
| 2013/0158557 A1 | 6/2013 | Komistek | |
| 2013/0197881 A1 | 8/2013 | Mansi et al. | |
| 2013/0211256 A1 | 8/2013 | Russell et al. | |
| 2014/0005562 A1* | 1/2014 | Bunch | A61B 5/046 600/518 |
| 2014/0088943 A1 | 3/2014 | Trayanova et al. | |
| 2014/0107510 A1 | 4/2014 | Bogun et al. | |
| 2014/0200575 A1* | 7/2014 | Spector | A61B 5/04017 606/40 |
| 2014/0241988 A1 | 8/2014 | Jalife | |
| 2014/0276152 A1* | 9/2014 | Narayan | A61B 5/0002 600/508 |
| 2014/0323882 A1 | 10/2014 | Ghosh et al. | |
| 2014/0329907 A1 | 11/2014 | Ye | |
| 2015/0042646 A1 | 2/2015 | Comaniciu et al. | |
| 2015/0216432 A1* | 8/2015 | Yang | A61B 5/7246 600/512 |
| 2015/0216434 A1* | 8/2015 | Ghosh | A61B 5/04085 600/509 |
| 2015/0216438 A1 | 8/2015 | Bokan et al. | |
| 2015/0313510 A1 | 11/2015 | Razavi et al. | |
| 2016/0005106 A1 | 1/2016 | Giraldez et al. | |
| 2016/0012592 A1 | 1/2016 | Chou et al. | |
| 2016/0022375 A1 | 1/2016 | Blake et al. | |
| 2016/0135702 A1 | 5/2016 | Perez | |
| 2016/0210435 A1* | 7/2016 | Neumann | G16H 50/50 |
| 2016/0262635 A1 | 9/2016 | McCullouch et al. | |
| 2016/0331337 A1* | 11/2016 | Ben-Haim | A61B 6/5217 |
| 2017/0027649 A1* | 2/2017 | Kiraly | A61B 90/37 |
| 2017/0079542 A1* | 3/2017 | Spector | A61B 5/0422 |
| 2017/0178403 A1 | 6/2017 | Krummen et al. | |
| 2017/0185740 A1 | 6/2017 | Seegerer et al. | |
| 2017/0209698 A1* | 7/2017 | Villongco | A61B 5/055 |
| 2017/0304005 A1 | 10/2017 | Maino et al. | |
| 2017/0319278 A1* | 11/2017 | Trayanova | A61B 34/10 |
| 2017/0367603 A1* | 12/2017 | Spector | A61B 5/04017 |
| 2018/0028265 A1 | 2/2018 | Azevedo Da Silva et al. | |
| 2018/0318606 A1 | 11/2018 | Robinson et al. | |
| 2019/0104951 A1* | 4/2019 | Valys | G16H 50/30 |
| 2019/0206127 A1 | 7/2019 | Krummen et al. | |
| 2019/0282821 A1 | 9/2019 | Masuda et al. | |
| 2020/0138394 A1 | 5/2020 | Vanden Berghe et al. | |
| 2020/0245935 A1 | 8/2020 | Krummen et al. | |

FOREIGN PATENT DOCUMENTS

| | | |
|---|---|---|
| WO | WO-2009079344 A1 | 6/2009 |
| WO | WO-2010042826 | 4/2010 |
| WO | WO-2010052303 A1 | 5/2010 |
| WO | WO-2010054409 | 5/2010 |
| WO | WO-2012055498 A1 | 5/2012 |
| WO | WO-2012109618 A2 | 8/2012 |

OTHER PUBLICATIONS

Villongco, Christopher T., et al. "Patient-specific modeling of ventricular activation pattern using surface ECG-derived vectorcardiogram in bundle branch block." Progress in biophysics and molecular biology 115.2-3 (2014): 305-313. (Year: 2014).*

Carrault, Guy, et al. "A model-based approach for learning to identify cardiac arrhythmias." Joint European Conference on Artificial Intelligence in Medicine and Medical Decision Making. Springer, Berlin, Heidelberg, 1999. (Year: 1999).*

Tobón, Catalina, et al. "Dominant frequency and organization index maps in a realistic three-dimensional computational model of atrial fibrillation." Europace 14.suppl_5 (2012): v25-v32. (Year: 2012).*

Horácek, B. Milan. "Value of simulated body surface potential maps as templates in localizing sites of ectopic activation for radiofrequency ablation." Physiological measurement 18.4 (1997): 373. (Year: 1997).*

Cobb, Leonard A., et al., "Changing incidence of out-of-hospital ventricular fibrillation, 1980-2000." Jama 288.23 (2002): 3008-3013.

Gonzales, Matthew J., et al., "Structural contributions to fibrillatory rotors in a patient-derived computational model of the atria." EP Europace 16.suppl 4 (2014): iv3-iv10.

Hren Rok, and Horácek, B. Milan. "Value of simulated body surface potential maps as templates in localizing sites of ectopic activation for radiofrequency ablation." Physiological measurement 18.4 (1997): 373-400.

(56) References Cited

OTHER PUBLICATIONS

Krishnamurthy, Adarsh, et al., "CRT Response is Greater in Patients With Larger Fraction of the Myocardium Performing Negative Regional Work." Circulation 128.Suppl 22 (2013): A11135-A11135, Abstract only.

Krishnamurthy, Adarsh, et al., "Patient-specific models of cardiac biomechanics." Journal of computational physics 244 (2013): 4-21.

Krummen, David E., et al., "Rotor stability separates sustained ventricular fibrillation from self-terminating episodes in humans." Journal of the American College of Cardiology 63.24 (2014): 2712-2721.

Nash, Martyn P., et al., "Evidence for multiple mechanisms in human ventricular fibrillation." Circulation 114.6 (2006): 536-542.

Taggart, Peter, et al., "Developing a novel comprehensive framework for the investigation of cellular and whole heart electrophysiology in the in situ human heart: Historical perspectives, current progress and future prospects."Progress in biophysics and molecular biology115.2-3 (2014): 252-260.

Ten Tusscher, K. H. W. J., et al., "A model for human ventricular tissue." American Journal of Physiology-Heart and Circulatory Physiology 286.4 (2004): H1573-H1589.

Tobón, Catalina, et al., "Dominant frequency and organization index maps in a realistic three-dimensional computational model of atrial fibrillation." Europace14.suppl 5 (2012): v25-v32.

Vadakkumpadan, Fijoy, et al., "Image-based estimation of ventricular fiber orientations for personalized modeling of cardiac electrophysiology." IEEE-TMI 31.5 (2012): 1051-1060.

Villongco, Christopher T., et al., "Patient-specific modeling of ventricular activation pattern using surface ECG-derived vectorcardiogram in bundle branch block." Progress in biophysics and molecular biology 115.2 (2014): 305-313.

Yokokawa, M. et al., "Automated analysis of the 12-lead electrocardiogram to identify the exit site of postinfarction ventricular tachycardia." Heart Rhythm Society vol. 9, No. 3, Mar. 2012: 330-334, (5 pages).

Aguado-Sierra, J., et al. "Patient-specific modeling of dyssynchronous heart failure: a case study." Progress in Biophysics and Molecular Biology, vol. 107 No. 1, 2011, pp. 147-155.

Alexander, D. C., et al. "Spatial Transformations of Diffusion Tensor Magnetic Resonance Images." IEEE Transactions on Medical Imaging, vol. 20 No. 11, 2001, pp. 1131-1139.

Aronszajn, N. "Theory of reproducing kernels." Transactions of the American Mathematical Society, vol. 68, 1950, pp. 337-404.

Arsigny, V., et al. "Log-Euclidean metrics for fast and simple calculus on diffusion tensors." Magnetic Resonance in Medicine: Official Journal of the Society of Magnetic Resonance in Medicine / Society of Magnetic Resonance in Medicine, vol. 56 No. 2, 2006, pp. 411-421.

Auricchio, A., et al. "Characterization of left ventricular activation in patients with heart failure and left bundle-branch block." Circulation, vol. 109, No. 9, 2004, pp. 1133-1139.

Bazan, V., et al., "Three-dimensional myocardial scar characterization from the endocardium: Usefulness of endocardial unipolar electroanatomic mapping." J Cardiovasc Electrophysiol 2019;30:427-437.

Berger, T., et al."Single-beat noninvasive imaging of cardiac electrophysiology of ventricular preexcitation."Journal of the American College of Cardiology, vol. 48, No. 10, 2006, pp. 2045-2052.

Burger, H. C., et al., "Head-Vector and Leads." British Head Journal, vol. 8, No. 3,1946, pp. 157-161.

Cao, Y., et al. "Large deformation diffeomorphic metric mapping of vector fields." Medical Imaging, IEEE Transactions, vol. 24, No. 9, 2005, pp. 1216-1230.

Chalil, S., et al., "Intraventricular Dyssynchrony Predicts Modality and Morbidity After Cardiac Resynchronization Therapy A Study Using Cardiovascular Magnetic Resonance Tissue Synchronization Imaging", Journal of The American College Of Cardiology, vol. 50, No. 3, pp. 243-252, XP029654014, ISSN: 0735-1097, DOI: 10.1016/J.JACC.2007.03.035.

Cluitmans, M. J. M., et al. "Inverse Reconstruction of Epicardial Potentials Improve by Vectorcardiography and Realistic Potentials." Computing in Cardiology, vol. 40, 2013, pp. 369-372.

Coronel, R., et al., "Right ventricular fibrosis and conduction delay in a patient with clinical signs of Brugada syndrome: a combined electrophysiological, genetic, histopathologic, and computational study." Circulation. 2005;112:2769-77.

Cortez, D.L. et al., "When deriving the spatial QRS-T angle from the 12-lead electrocardiogram, which transform is more Frank: regression or inverse Dower?" Journal of Electrocardiology 43.4 (2010): 302-309.

Daubert, J.-C., et al. "2012 EHRA/HRS expert consensus statement on cardiac resynchronization therapy in heart failure: implant and follow-up recommendations and management." Heart Rhythm: The Official Journal of the Heart Rhythm Society, vol. 9 No. 9, 2012, pp. 1524-1576.

De Boeck, B.W.L., et al., "Septal rebound stretch reflects the functional substrate to cardiac resynchronization therapy and predicts volumetric and neurohormonal response." Eur J Head Fail. 2009;1 1(9):863-71, 9 pages.

De Vito, E., et al. "Adaptive kernel methods using the balancing principle." Foundations of Computational Mathematics, vol. 10, No. 4, 2010, pp. 455-479.

De Vito, E., et al. "Learning from examples as an inverse problem." Journal of Machine Learning Research, vol. 6, 2005, pp. 883-904.

Dossel, O., et al. "Imaging of bioelectric sources in the head using a cellular automaton model." Conference Proceedings: Annual International Conference of the IEEE Engineering in Medicine and Biology Society. IEEE Engineering in Medicine and Biology Society. Conference, 2005, pp. 1067-1070.

Edenbrandt, L., et al., "Vectorcardiogram synthesized from a 12-lead ECG: superiority of the inverse Dower matrix." Journal of Electrocardiology, vol. 21, No. 4, 1988, pp. 361-367.

Engl, H., et al. "Regularization of Inverse Problems." Mathematics and Its Application, vol. 375, 1996.

Epstein A.E., et al., ACC/AHA/HRS 2008 Guidelines for Device-Based Therapy of Cardiac Rhythm AbnormalitiesPractice Guideline. J Am Coll Cardiol. 2008;51:21.

Epstein A.E., et al., American College of Cardiology F, American Head Association Task Force on Practice G and Head Rhythm S. 2012 ACCF/AHA/HRS focused update incorporated into the ACC/AHA/HRS 2008 guidelines for device-based therapy of cardiac rhythm abnormalities: a report of the American College of Cardiology Foundation/American Head Association Task Force on Practice Guidelines and the Head Rhythm Society. J Am Coll Cardiol. 2013;61:e6-75.

Fillard, P., et al., "Clinical DT-MRI estimation, smoothing, and fiber tracking with log-Euclidean metrics." IEEE Transactions on Medical Imaging, vol. 26, No. 11, 2007, pp. 1472-1482.

Gersh B.J., et al., 2011 ACCF/AHA Guideline for the Diagnosis and Treatment of Hypertrophic Cardiomyopathy: a report of the American College of Cardiology Foundation/American Heart Association Task Force on Practice Guidelines. Developed in collaboration with the American Association for Thoracic Surgery, American Society of Echocardiography, American Society of Nuclear Cardiology, Heart Failure Society of America, Heart Rhythm Society, Society for Cardiovascular Angiography and Interventions, and Society of Thoracic Surgeons. Journal of the American College of Cardiology. 2011;58:e212-60.

Gold, M. R., et al. "The relationship between ventricular electrical delay and left ventricular remodelling with cardiac resynchronization therapy." European Heart Journal, vol. 32, No. 20, 2011, pp. 2516-2524.

Golub, G. H., et al. "Singular Value Decomposition and Least Squares Solutions." Numerische Mathematik, vol. 14, 1970, pp. 403-420.

Gonzales, M. J., et al. "A three-dimensional finite element model of human atrial anatomy: new methods for cubic Hermite meshes with extraordinary vertices." Medical Image Analysis, vol. 17 No. 5, 2013, pp. 525-537.

Greensite, F., et al., "An improved method for estimating epicardial potentials from the body surface." IEEE Transactions on Bio-Medical Engineering, vol. 45, No. 1, 1998, pp. 98-104.

(56) References Cited

OTHER PUBLICATIONS

Guillem, M. S., et al. "Derivation of orthogonal leads from the 12-lead ECG. Accuracy of a single transform for the derivation of atrial and ventricular waves." In Computers in Cardiology, 2006, pp. 249-252.
Gulrajani, R.M., "The forward and inverse problems of electrocardiography." IEEE Engineering in Medicine and Biology Magazine 17.5 (1998): 84-101.
Haissaguerre, M., et al., "Localized Structural Alterations Underlying a Subset of Unexplained Sudden Cardiac Death." Circ Arrhythm Electrophysiol 2018;11:e006120.
Han, C., et al. "Noninvasive reconstruction of the three-dimensional ventricular activation sequence during pacing and ventricular tachycardia in the canine heart." American Journal of Physiology. Heart and Circulatory Physiology, vol. 302, No. 1, 2012, pp. H244-H252.
Han, C., et al. "Noninvasive reconstruction of the three-dimensional ventricular activation sequence during pacing and ventricular tachycardia in the rabbit heart." Conference Proceedings: Annual International Conference of the IEEE Engineering in Medicine and Biology Society, 2011, pp. 1684-1687.
He, B., et al. "Noninvasive three-dimensional activation time imaging of ventricular excitation by means of a heart-excitation model." Physics in Medicine and Biology, vol. 47, No. 22, 2002, pp. 4063-4078.
Helm, R.H., et al., "Cardiac Dyssynchrony Analysis Using Circumferential Versus Longitudinal Strain: Implications for Assessing Cardiac Resynchronization." Circulation. 111 (2005), pp. 2760-2767, 8 pages.
Ho, G., et al., "Rotors exhibit greater surface ECG variation during ventricular fibrillation than focal sources due to wavebreak, secondary rotors, and meander." J Cardiovasc Electrophysiol. 2017;28:1158-1166.
Kerckhoffs, R., et al., "Ventricular dilation and electrical dyssynchrony synergistically increase regional mechanical non-uniformity but not mechanical dyssynchrony: a computational model." Circulation: Heart Failure (2010): CIRCHEARTFAILURE-109.
Kimeldorf, G., et al., "Some results on Tchebycheffian spline functions." Journal of Mathematical Analysis and Applications, vol. 33, 1971, pp. 82-95.
Kindermann, S., et al., "On the convergence of the quasi-optimality criterion for (iterated) Tikhonov regularization." Inverse Problems and Imaging, vol. 2, No. 2, 2008, pp. 291-299.
Kirn, Borut, et al., "Mechanical discoordination rather than dyssynchrony predicts reverse remodeling upon cardiac resynchronization." Am J Physiol Heart Circ Physiol. 295, Aug. 2008;295(2):H640-6, 7 pages.
Kors, J. A., et al. "Reconstruction of the Frank vectorcardiogram from standard electrocardiographic leads: diagnostic comparison of different methods." European Heart Journal, vol. 11, No. 12, 1990, pp. 1083-1092.
Krummen, D.E., et al., "Mechanisms of human atrial fibrillation initiation: clinical and computational studies of repolarization restitution and activation latency." Circ Arrhythm Electrophysiol 2012;5:1149-59.
Krummen, D.E., et al., "Modifying Ventricular Fibrillation by Targeted Rotor Substrate Ablation: Proof-of-Concept from Experimental Studies to Clinical VF." J Cardiovasc Electrophysiol 2015;26:1117-26.
Leclercq, C., et al., "Systolic Improvement and Mechanical Resynchronization Does Not Require Electrical Synchrony in the Dilated Failing Heart With Left Bundle-Branch Block." Circulation, 106 (2002). pp. 1760-1763, 4 pages.
Li, G., et al., "Localization of the site of origin of cardiac activation by means of a heart-model-based electrocardiographic imaging approach." IEEE Transactions on Bio-Medical Engineering, vol. 48, No. 6, 2001, pp. 660-669.
Lin, T., et al. "Implant electrical characteristics predict response to cardiac resynchronization therapy." World Journal of Cardiovascular Diseases, 2014.
Liu, C., et al. "Estimation of global ventricular activation sequences by noninvasive 3-dimensional electrical imaging: validation studies in a swine model during pacing." Journal of Cardiovasc Electrophysiol, vol. 19, No. 5, 2009, pp. 535-540.
McVeigh, E.R., et al., "Regional myocardial strain measurements from 4DCT in patients with normal LV function." J Cardiovasc Comput Tomogr 2018;12:372-378.
Messinger-Rapport, B. J., et al., "Regularization of the inverse Problem in Electrocardiography: A Model Study." Mathematical Biosciences, vol. 89,1998, pp. 79-118.
Messnarz, B., et al., "A new spatiotemporal regularization approach for reconstruction of cardiac transmembrane potential patterns." IEEE transactions on Biomedical Engineering 51.2 (2004): 273-281.
Micchelli, C. A., et al., "Learning the kernel function via regularization." Journal of Machine Learning Research, vol. 6, 2005, pp. 1099-1125.
Myerburg R.J., et al., "Interpretation of outcomes of antiarrhythmic clinical trials: design features and population impact." Circulation. 1998;97:1514-21.
Narayan, S.M., et al., "Steep restitution of ventricular action potential duration and conduction slowing in human Brugada syndrome." Heart Rhythm. 2007;4:1087-9.
Naumova, V., et al. "A meta-learning approach to the regularized learning—case study: Blood glucose prediction." Neural Networks, vol. 33, 2012, pp. 181-193.
Naumova, V., et al. "Extrapolation in variable RKHSs with application to the blood glucose reading." Inverse Problems, vol. 27, No. 7, 2011, pp. 1-13.
Niederer, S.A., et al., "Analyses of the Redistribution of Work following Cardiac Resynchronisation Therapy in a Patient Specific Model." PLoS ONE 7(8), 2012, 9 pages.
O'Hanlon, R., et al., "Prognostic significance of myocardial fibrosis in hypertrophic cardiomyopathy." Journal of the American College of Cardiology. 2010;56:867-74.
Oster, H. S., et al., "The use of temporal information in the regularization of the inverse problem of electrocardiography." IEEE Transactions on Bio-Medical Engineering, vol. 39, No. 1,1992, pp. 65-75.
Oster, H.S., et al., "Noninvasive electrocardiographic imaging: reconstruction of epicardial potentials, electrograms, and isochrones and localization of single and multiple electrocardiac events." Circulation. 1997;96:1012-24.
Pfeifer, B., et al. "Patient-specific volume conductor modeling for non-invasive imaging of cardiac electrophysiology." The Open Medical Informatics Journal, vol. 2, 2008, pp. 32-41.
Ploux, S., et al. "Noninvasive electrocardiographic mapping to improve patient selection for cardiac resynchronization therapy: beyond QRS duration and left bundle branch block morphology." Journal of the American College of Cardiology, vol. 61, No. 24, 2013, pp. 2435-2443.
Ramanathan, C., et al. "Noninvasive electrocardiographic imaging for cardiac electrophysiology and arrhythmia." Nature Medicine, vol. 10, No. 4, 2004, pp. 422-428.
Ramanathan, C., et al. "Noninvasive Electrocardiographic Imaging (ECGI): Application of the Generalized Minimal Residual (GMRes) Method." Annals of Biomedical Engineering, vol. 31, No. 8, 2003, pp. 981-994.
Rodriguez, L.-M., et al. "Variable patterns of septal activation in patients with left bundle branch block and heart failure." Journal of Cardiovascular Electrophysiology, vol. 14, No. 2, 2003, pp. 135-141.
Rotter, M., et al. "Reduction of fluoroscopy exposure and procedure duration during ablation of atrial fibrillation using a novel anatomical navigation system." European Heart Journal, vol. 26, No. 14, 2005, pp. 1415-1421.
Rudy, Y. "Noninvasive electrocardiographic imaging of arrhythmogenic substrates in humans." Circulation Research, vol. 112, No. 5, 2013, pp. 863-874.
Schreck, D. M.,et. al. "Statistical methodology: VI. Mathematical modeling of the electrocardiogram using factor analysis." Academic Emergency Medicine, vol. 5, No. 9, 1998, pp. 929-934.

(56) References Cited

OTHER PUBLICATIONS

Seo, Y., et al., "Mechanical dyssynchrony assessed by speckle tracking imaging as a reliable predictor of acute and chronic response to cardiac resynchronization therapy." Journal of the American Society of Echocardiography 22.7 (2009): 839-846.
Singh, J. P., et al. "Left ventricular lead electrical delay predicts response to cardiac resynchronization therapy." Heart Rhythm, vol. 3, No. 11, 2006, pp. 1285-1292.
Stecker, E.C., et al., "Population-based analysis of sudden cardiac death with and without left ventricular systolic dysfunction: two-year findings from the Oregon Sudden Unexpected Death Study." J Am Coll Cardiol. 2006;47:1161-6.
Stevenson, W.G., et al., "Identification of reentry circuit sites during catheter mapping and radiofrequency ablation of ventricular tachycardia late after myocardial infarction." Circulation 1993;88:1647-70.
Strauss, D. G., et al. "Defining left bundle branch block in the era of cardiac resynchronization therapy." *The American Journal of Cardiology*, vol. 107, No. 6, 2011, pp. 927-934.
Sweeney, M. O., et al. "Analysis of ventricular activation using surface electrocardiography to predict left ventricular reverse volumetric remodeling during cardiac resynchronization therapy." *Circulation*, vol. 121, No. 5, 2010, pp. 626-634.
ten Tusscher, K.H.W.J., et al., "Alternans and spiral breakup in a human ventricular tissue model. American Journal of Physiology." Heart and Circulatory Physiology, vol. 291, 2006, pp. H1088-H1100.
Tikhonov, A. N., et al. *Solutions of ill-posed problems*. Winston, (p. 258), 1997.
Tikhonov, A. N., et al., "Use of the regularization methods in non-linear problems." USSR Computational Mathematics and Mathematical Physics, vol. 5,1965.

Van der Graaf, A. W. M., et al. "Noninvasive imaging of cardiac excitation: current status and future perspective. Annals of Noninvasive Electrocardiology." *The Official Journal of the International Society for Holter and Noninvasive Electrocardiology, Inc*, vol. 19, No. 2, 2014, pp. 105-113.
van Deursen, C. J., et al. "Vectorcardiography as a tool for easy optimization of cardiac resynchronization therapy in canine left bundle branch block hearts." *Circulation: Arrhythmia and Electrophysiology*, vol. 5, No. 3, 2012, pp. 544-552.
Vaquero, M., et al. "Cardiac Fibrillation: From Ion Channels to Rotors in the Human Heart." *Heart Rhythm: The Official Journal of the Heart Rhythm Society*, vol. 5, No. 6, 2008, pp. 872-879.
Varma, N., et al. "Electrocardiographic imaging of patients with heart failure with left bundle branch block and response to cardiac resynchronization therapy." *Journal of Electrocardiology*, vol. 40,2007, pp. S174-S178.
Wang, Y., et al. "Noninvasive electroanatomic mapping of human ventricular arrhythmias with electrocardiographic imaging." *Science Translational Medicine*, vol. 3, No. 98, 2011, p. 98ra84.
Wittkampf, F. H., et al. "LocaLisa new technique for real-time 3-dimensional localization of regular intracardiac electrodes." *Circulation*, vol. 99, No. 10, 1999, pp. 1312-1317.
Yamashita, Y. "Theoretical studies on the inverse problem in electrocardiography and the uniqueness of the solution." *Biomedical Engineering, IEEE Transactions*, vol. 11, 1982, pp. 719-725.
Yushkevich, P. A., et al. "User-guided 3D active contour segmentation of anatomical structures: significantly improved efficiency and reliability." *NeuroImage*, vol. 31, No. 3, 2006, pp. 1116-1128.
Zhang, J., et al., "Cardiac electrophysiological substrate underlying the ECG phenotype and electrogram abnormalities in Brugada syndrome patients." Circulation. 2015;131:1950-9.
Zhang, X., et al. "Noninvasive three-dimensional electrocardiographic imaging of ventricular activation sequence." *AJP-Heart Circulatory Physiology*, vol. 289, 2005, pp. 2724-2732.

* cited by examiner

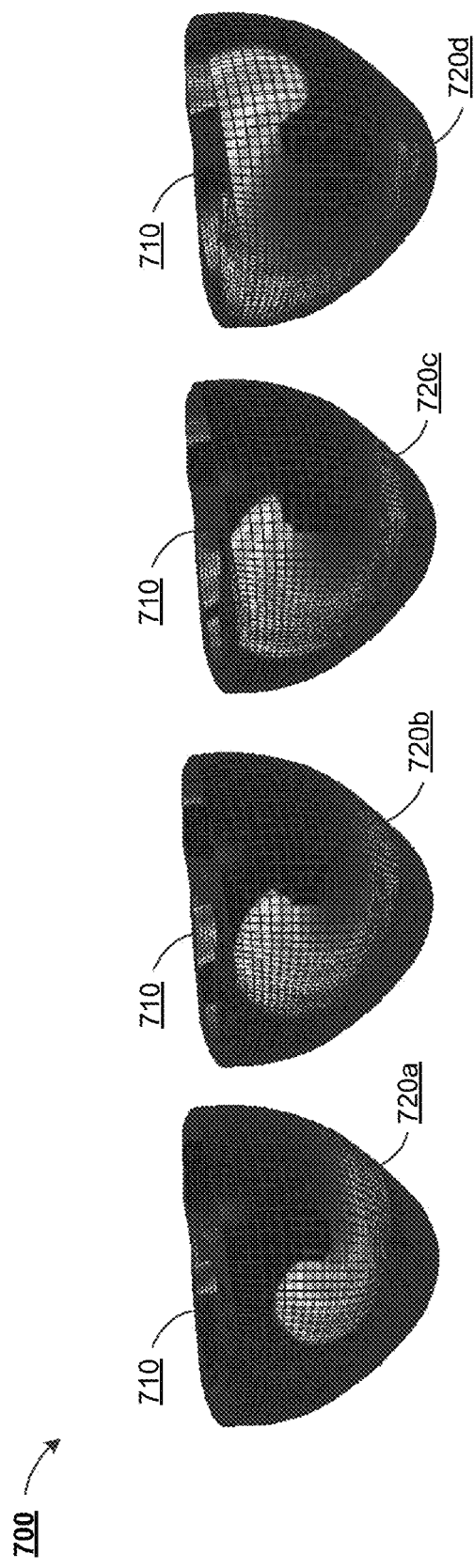
FIG. 7A
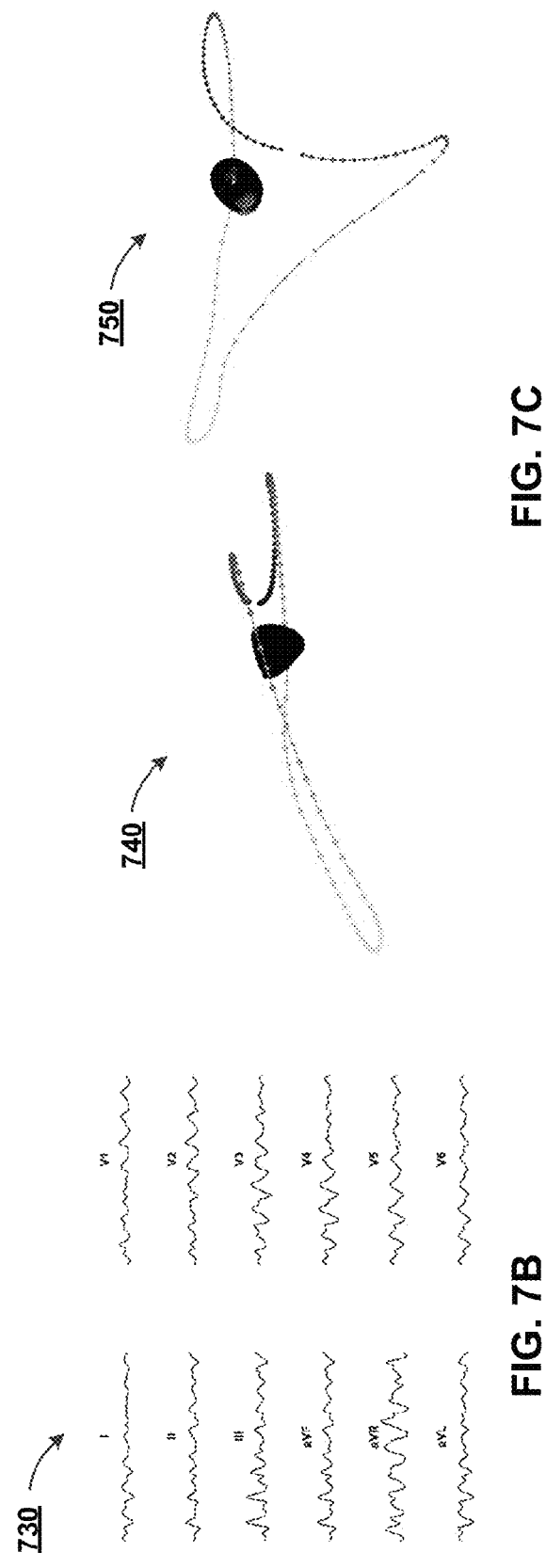
FIG. 7B
FIG. 7C

COMPUTATIONAL LOCALIZATION OF FIBRILLATION SOURCES

CROSS REFERENCE TO RELATED APPLICATIONS

This application is a continuation application of U.S. patent application Ser. No. 16/295,934, filed on Mar. 7, 2019, entitled "COMPUTATIONAL LOCALIZATION OF FIBRILLATION SOURCES," which is a continuation application of U.S. patent application Ser. No. 15/389,245, filed on Dec. 22, 2016, now U.S. Pat. No. 10,319,144, entitled "COMPUTATIONAL LOCALIZATION OF FIBRILLATION SOURCES," which claims priority to U.S. Provisional Patent Application No. 62/271,113, filed on Dec. 22, 2015, and entitled "COMPUTATIONAL LOCALIZATION OF VENTRICULAR FIBRILLATION SOURCES," the disclosures of these applications are incorporated herein by reference.

TECHNICAL FIELD

The subject matter described herein relates to computational localization of fibrillation sources, and more particularly, identification of ventricular fibrillation (VF) and/or atrial fibrillation (AF) sources.

BACKGROUND

Ventricular fibrillation (VF) and atrial fibrillation (AF) can cause symptoms, morbidity (syncope or stroke), and mortality. Stable electrical rotors, recurring electrical focal sources, and other mechanisms are important drivers of sustained and/or clinically significant episodes of VF/AF. In order to treat VF/AF, therapeutic ablation, radiofrequency (RF), cryogenic, ultrasound, and/or external radiation sources can be used to target and/or eliminate these mechanisms. The ability to map the sustaining mechanisms for VF and/or AF using noninvasive methods would provide significant benefit in the management of such arrhythmias.

Current methods for reliably identifying the location of VF/AF-sustaining mechanisms (e.g., rotors or focal sources) are presently suboptimal. They often require an invasive procedure, the insertion of expensive 64-electrode basket catheters, and/or mapping arrhythmias using an expensive, difficult to obtain/manufacture, and cumbersome body surface vest, which may interfere with the placement of defibrillator pads. Therefore, such procedures are expensive, time consuming, and potentially hazardous to patients. Accordingly, methods for identifying the existence and/or location of fibrillation sources with less costly and/or less invasive procedures may provide significant clinical benefit.

SUMMARY

In some aspects, a method, computer program product and system are provided. In an implementation, a system for computational localization of fibrillation sources is provided. The system can include (or otherwise utilize) at least one processor and/or memory, which can be configured to perform operations including generating a representation of electrical activation of a patient's heart and comparing, based on correlation, the generated representation against one or more stored representations of hearts to identify at least one matched representation of a heart. The operations can further comprise generating, based on the at least one matched representation, a computational model for the patient's heart, wherein the computational model includes an illustration of one or more fibrillation sources in the patient's heart. Additionally, the operations can comprise displaying, via a user interface, at least a portion of the computational model.

In some aspects, the generated representation and/or the one or more stored representations can include three-dimensional data (e.g., can be 3D models). In some aspect, the generated representation and/or the one or more stored representations can comprise vectorcardiograms. Comparing the representations can include determining, for each of the one or more stored representations, a correlation factor between the generated representation and the stored representation, and the at least one matched representation can be identified as the stored representation(s) with a highest correlation factor.

In some variations, the operations can further comprise generating a plurality of computational heart models with varying shapes, geometries, fiber orientations, scars, fibrillation source types, and fibrillation source locations. The operations can also comprise filtering the plurality of computational heart models based on a shape or scarring of the patient's heart to identify a filtered set, and/or selecting the one or more stored representations for the comparing based on the filtered set. In various implementations, the filtering can be based on computerized tomography imaging data, magnetic resonance imaging data, echocardiography data, X-ray data, fluoroscopy data, and/or the like.

In some variations, the computational model comprises one or more of a left atrium, a right atrium, a left ventricle, and a right ventricle, and/or the one or more fibrillation sources can be mapped to one or more of the left atrium, the right atrium, the left ventricle, and the right ventricle. The one or more fibrillation sources can include a rotor or a focal source, or some other source of ventricular fibrillation or atrial fibrillation. In some variations, the computational model includes a three-dimensional mesh in a heart shape and/or a finite state fibrillatory source map of cardiac electrical activations mapped to the mesh.

In some variations, the operations can further comprise generating electrocardiogram plots based on the patient's heart, and/or generating the vectorcardiogram based on the electrocardiogram plots. In some variations, the operations can further comprise generating a second computational model for the patient's heart based on the (original) computational model, wherein the second computational model is generated to include a number of fibrillation sources that is less than the one or more fibrillation sources. A side-by-side comparison of the computational model and the second computational mode can be displayed via a user interface. In some aspects, the second computational model can be generated by removing one of the one or more fibrillation sources from the computational model. In some variations, the operations can further include determining a change in fibrillation between the computational model and the second computational model.

Implementations of the current subject matter can include systems and methods consistent with the present description, including one or more features as described, as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, show certain aspects of the subject matter disclosed herein and, together with the description, help explain some of the principles associated with the disclosed implementations. In the drawings.

FIG. 7A depicts a biventricular computational model with VF at different time points, in accordance with some example implementations;

FIG. 7B depicts a graph of computed EKG tracings over a time interval, in accordance with some example implementations;

FIG. 7C depicts computed VCG tracings over the time interval, in accordance with some example implementations;

When practical, similar reference numbers denote similar structures, features, or elements.

DETAILED DESCRIPTION

As noted above, it can be desirable to identify the existence and/or location of fibrillation sources with less costly and/or less invasive procedures/methods. Accordingly, non-invasive systems and methods for identifying the presence and/or location of rotors or focal sources (collectively referred to herein as "fibrillation mechanisms") in patients with ventricular fibrillation (VF) or atrial fibrillation (AF) are described. In some implementations, readily-available twelve-lead electrocardiogram (EKG) sensor devices can be applied to the surface of a patient's skin, instead of single-use 64-electrode basket catheters that require surgical implantation and/or external electrocardiogram ("EKG" or "ECG") vests using twenty or more electrodes, which are highly specialized and costly.

Figure 1:
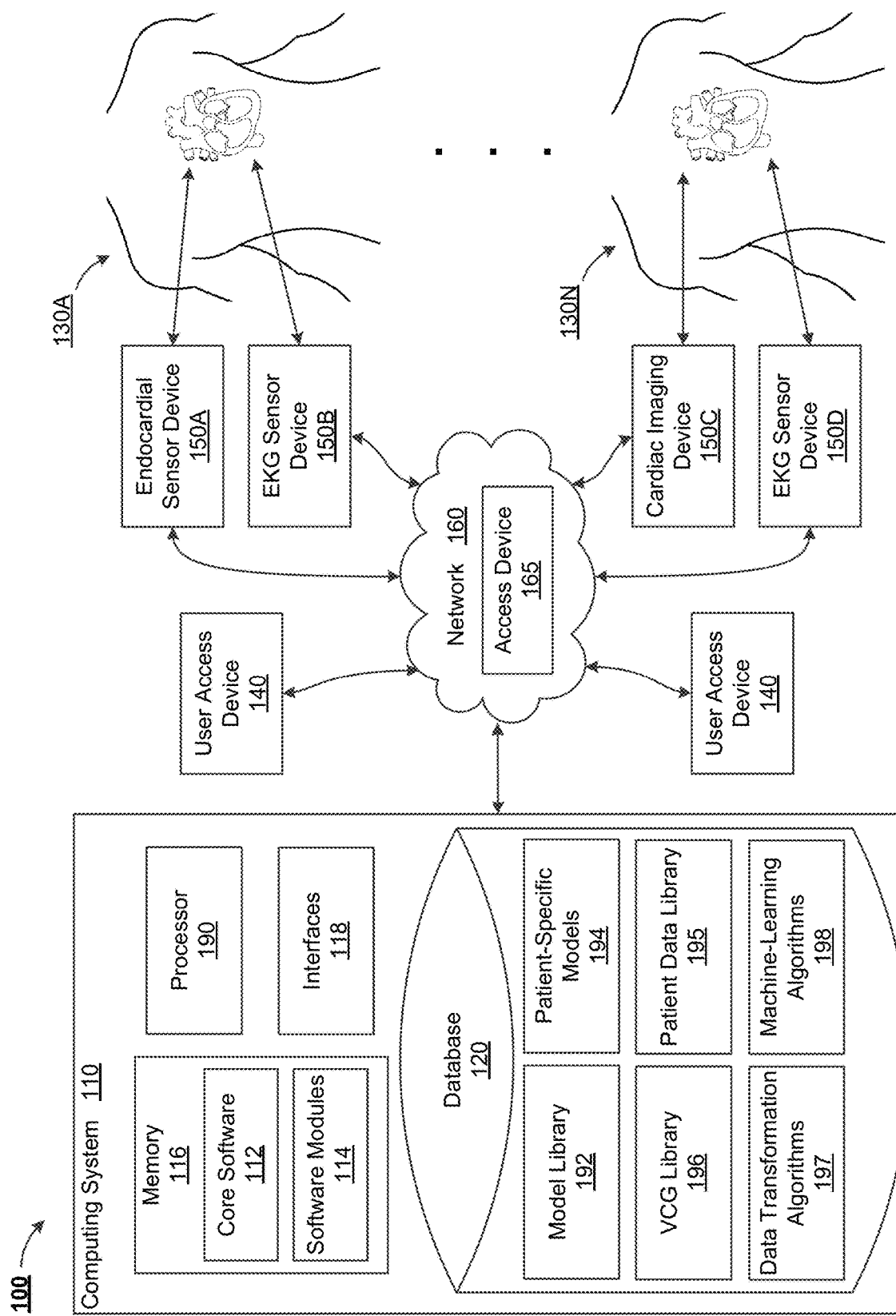
FIG. 1 depicts a block diagram of a system for computational localization of fibrillation sources, in accordance with some example implementations.

FIG. 1 illustrates a functional block diagram of a system 100 in which features consistent with the described subject matter may be implemented. As illustrated, the system 100 can include a computing system 110 capable of communicating with one or more user access devices 140 and/or one or more sensor devices 150A-D (collectively referred to as sensor devices 150). In some aspects, the computing system 100 can utilize one or more interfaces 118 for communication. Communication among the devices in the system 100 can be through the use of direct communications, such as through the use of a wireless connection like Bluetooth, near-field communication (NFC), ZigBee, WiFi, some combination thereof, and/or the like. Additionally or alternatively, communication among the devices in the system 100 can be through the use of a hard wired connection, such as universal serial bus (USB) and/or the like. Communication can additionally or alternatively occur through indirect communications, such as over a network 160, which can include a local area network, a wide area network, a wireless network, the Internet, some combination thereof, and/or the like.

Communication over the network 160 can utilize a network access device 165, such as a base station, a Node B, an evolved Node B (eNB), an access nodes (ANs), a hotspot, and/or the like. In some aspects, any of the user access devices 140 can include personal computers, desktop computers, laptops, workstations, cell phones, digital media devices, smart phones, smart watches, PDAs (personal digital assistants), tablets, hardware/software servers, sensors, sensor devices, terminals, access terminals (ATs), mobile stations, user equipment (UE), subscriber units, and/or the like. In some aspects, any of the sensor devices 150 can include EKG sensors/devices, vectorcardiogram (VCG) sensors/devices, heart imaging devices, and/or the like. In some implementations, heart imaging devices can include one or more of computerized tomography (CT or CAT) scan devices, magnetic resonance imaging (MRI) scan devices, sestamibi scan devices, thallium scan devices, multi-gated acquisition scan devices, X-ray devices, echocardiography devices, fluoroscopy devices, and/or the like. In various implementations, data (e.g., heart imaging data) can be provided and/or a respective device (e.g., heart imaging device) may not be present. Wired or wireless communication among the computing system 110, user access devices 140, and/or sensor devices 150 can occur according to various protocols and/or access technologies (e.g., Global System for Mobile Communication (GSM), Universal Mobile Telecommunications System (UMTS), technologies developed by IEEE such as WiFi and/or Bluetooth, technologies developed by the Third Generation Partnership Project (3GPP) or 3GPP2 such as Long Term Evolution (LTE) and/or CDMA2000, etc.).

At least a portion of the illustrated system 100 may include hardware and/or software that interacts with stored data, models, algorithms, etc., and/or receives, transmits, defines, creates, and/or updates data. As illustrated, the computing system 110 can include a processor 190, which can be used to manage/control the operation of the computing system 110. As further illustrated, the computing system 110 can include core software 112 and/or one or more software modules 114. The core software 112 can provide one or more features of a high-level programming software system. The software modules 114 can provide more specialized functionality. For example, the core software 112 and/or software modules 114 can include sensor management and/or data processing functionality. In some aspects, the core software 112 or other similar software/hardware can be capable of accessing a database layer, such as the database 120. The database 120 can store any kind of data, potentially including but not limited to data retrieved from sensor devices 150, computational models, EKG data, VCG data, machine learning algorithms, data transformation algorithms, and/or the like.

For example, as illustrated, the database 120 can include a model library 192, patient-specific models 194, a patient data library 195, a VCG library 196, data transformation algorithms 197, and/or machine learning algorithms 198. The model library 192 can hold a plurality of computational models of hearts, portions of hearts, other organs, and/or the like. The computational models in the model library 192 can be high-resolution (e.g., greater than about 500,000 degrees of freedom) finite element models. At least a portion of the computational models can be generated through incorporating the Fenton-Karma, Bueno-Cherry-Fenton, ten Tussher-Noble, or a similar, detailed ionic model of the human ventricular or atrial action potential during simulated VF or AF, respectively.

The patient-specific models 194 can include computational models similar to the models in the model library 192, but the models in the patient-specific models 194 can be generated based upon data from actual patients. For example, as illustrated, an endocardial sensor device 150A can be applied to record data from the interior of a heart in a patient 130A. At the same (or approximately the same) time, an EKG sensor 150B can be applied to the exterior of the patient 130A to record EKG readings. Based upon the combination of these readings, one or more patient-specific models 194 can be generated and stored. In some implementations, patient-specific models 194 can additionally or alternatively be based upon CT scan data, MRI scan data, sestamibi scan data, thallium scan data, multi-gated acquisition scan data, fluoroscopy data, x-ray data, echocardiography data, and/or other cardiac imaging data, which can be used to identify the shape, scarring, etc. of the heart of the patient 130N.

The VCG library 196 can include VCG data for the computational models of the model library 192 and/or the patient-specific models 194. For example, VCG models can be simulated based on the computational models in the model library 192 (e.g., based upon EKG data associated with each model). In some implementations, VCG models can include three-dimensional tracings of electrical activity in a heart or some portion thereof. In some aspects, the VCG data can include temporospatial VCG data. The VCG data in the VCG library 196 may serve as diagnostic templates against which VCGs constructed from patient data can be matched. For example, this VCG library data can be compared with VCG data from a patient to identify the location(s) of VF/AF sources within the patient. For example, as illustrated, the EKG sensor device 150D can obtain EKG data from patient 130N. This EKG data can be used to generate VCG data, and the generated VCG data can be compared against the VCG data from the VCG library 196. Based upon the level of correlation among these data sets, VF/AF sources can be identified, as described herein. In some implementations, VCG data from the VCG library 196 can be (pre)filtered for comparison based upon physical characteristics (e.g., shape, scars, etc.) of the heart of the patient 130N, which can be determined based upon data obtained through a cardiac imaging device 150C, which can include a CT scan device, an MRI scan device, an echocardiography device, and/or the like. In some implementations, the data within the VCG library 196 can additionally/alternatively be stored within the model library 192. For example, each computational heart model can include or be associated with VCG data.

Figure 12:
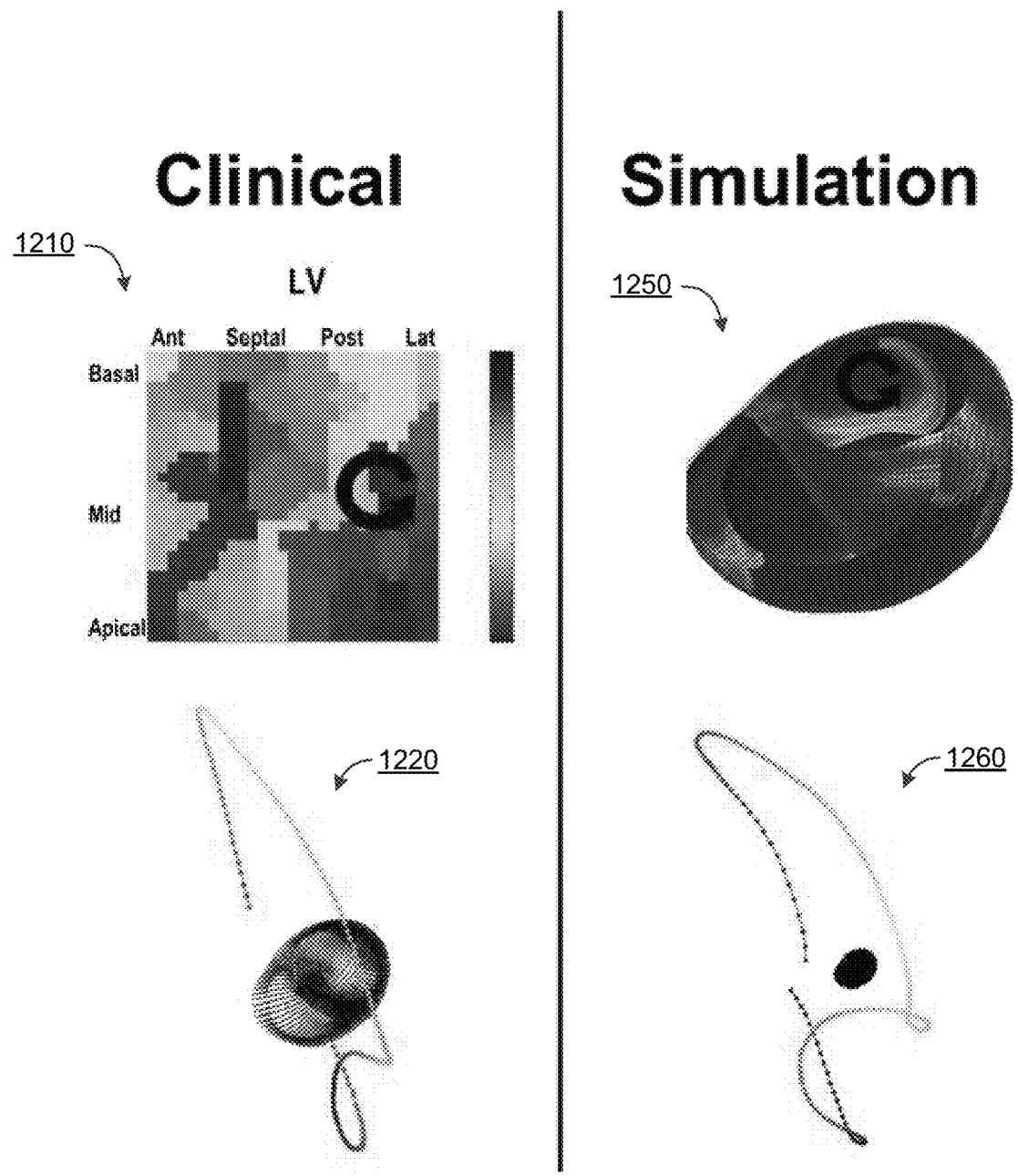
FIG. 12 depicts a simulated VCG and a measured human VCG of a rotor in the same anatomical position, in accordance with some example implementations.

In some implementations, the computational models within the model library 192 can be generated and/or verified based upon the patient specific models 194. For example, VCGs in the VCG library 196 may be validated by comparing them with human VCGs, which can be obtained from the patient-specific models 194. For example, FIG. 12 shows a comparison of VCGs 1220, 1260, generated based on a human rotor 1210 and a simulated rotor 1250, from the same ventricular location. In some aspects, the human rotor 1210 can be a VF source in a patient. As illustrated, the rotor can be in a mid-ventricular, postero-lateral position within the left ventricle, and/or rotating in a counterclockwise direction when viewed from the endocardium. The corresponding first VCG 1220 illustrates a clinical VCG loop for this patient, for a particular cycle of VF.

In some aspects, the second VCG 1260 illustrates a simulated VCG loop, which closely approximates the clinical VCG 1220 (e.g., for the same cycle of VF). The second VCG 1260 can be stored within and/or retrieved from the VCG library 196. The corresponding computer-simulated rotor 1250 can simulate the VF source indicated by the data from the VCG 1260. As illustrated, the location of the simulated VF source rotor 1250 can also be located in the mid-ventricular, postero-lateral position within the left ventricle, and/or rotate in a counterclockwise direction when viewed from the endocardium. As illustrated, the VCGs 1220, 1260 are color-coded based on timing information.

Referring back to FIG. 1, in some aspects, the VCG in the patient-specific models 194 can be constructed from an existing human data set of surface EKGs, which can be stored in and/or provided from the patient data library 195, with known rotor and focal source locations identified using concurrent electrode invasive endocardial recordings taken from patients with induced VF.

In some aspects, the robustness of the patient specific models 194 can increase the accuracy and/or value of the model library 192, which can increase the likelihood of identifying VF/AF sources within a patient 130 and/or the accuracy of determining the specific location of the VF/AF sources within a heart of a patient 130. The machine-learning algorithms 198 can be trained based upon the patient-specific models 194 to generate algorithms for detecting VF/AF within a patient based upon receiving EKG sensor data, CT scan data, VCGs, and/or the like. For example, correlated EKG data and VCGs may be used to train machine-learning algorithms to identify VF/AF mechanisms and loci. In some example embodiments, an algorithm for deriving diagnostic criteria to predict the presence and location of VF/AF rotors can be provided. To this end, automated diagnostic tools may be provided to automatically compare VCGs computed from surface EKGs of patients with VF/AF against diagnostic templates (e.g., the VCG library 196) to identify the VF/AF mechanism(s) and location(s) using statistical classification and/or machine learning techniques.

In some implementations, data transformation algorithms 197 can be used to standardize EKG and/or VCG data measured from a patient 130A to account for inter-patient differences in thoracic dimensions, lung geometry, extent of musculature, body fat composition, and/or other factors which may affect surface electrode measurements, using statistical classification and/or machine learning techniques.

In some implementations, the model library 192, the patient-specific models 194, the VCG library 196, the machine learning algorithms 198, the data transformation algorithms 197, and/or the patient data library 195 can be specific to a VF/AF mechanism. For example, the model library 192 and the patient-specific models 194 can include models for rotors and separate models for focal sources. Accordingly, the VCG library 196 can include VCGs based on rotors and separate VCGs based on focal sources. As rotors and focal sources materialize in different ways within VCGs, using separate sets of models/VCGs can be used to identify the mechanism, in addition to its location.

In some aspects, the core software 112 can be configured to load the information from the database 120 to memory 116 (e.g., main memory) in response to receipt of a instructions, data, or a query initiated by a user or computer system through one or more sensor devices 150, user access devices 140, and/or the like. Although the database 120 is illustrated as being located within the computing system, in various implementations, at least a portion of the database 120 can be separate from the computing system 110.

In some aspects, one or more of the software modules 114 can be configured to utilize data stored in the memory 116, data stored in the database 120, and/or data otherwise accessible to the computing system 110. In some aspects, the computing system 110 can be capable of utilizing external software, which can provide additional functionalities or services which may not be available at the computing system 110. In some aspects, the external software may include cloud services. In some aspects, the computing system 110 can aggregate or otherwise provide a gateway via which users can access functionality provided by external software. In some implementations, the database 120 and/or the contents thereof can be located across one or more servers, and/or communication among the computing system 110, the user access devices 140, and/or the sensor devices 150 can occur over the network 160.

In some aspects, the database 120 may be physically stored in a hardware server or across a plurality of hardware servers. In some aspects, the system 100 may be implemented as a cloud-based system and/or a data processing system.

Figure 2A:
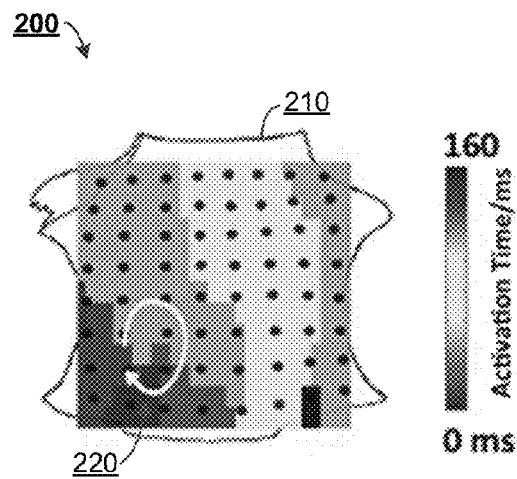
FIG. 2A depicts a map of activation time in a patient's right atrium, in accordance with some example implementations.

FIG. 2A depicts a fibrillatory source activation map 200 (in milliseconds according to the colored scale) in a patient's right atrium 210, in accordance with some example implementations. As illustrated, longer and/or more sustained activation of the right atrium 210 can rotate around a source 220. This source 220 can be regarded as a source of AF, and more particularly, a rotor. In some aspects, a rotor can be regarded as an organizing center for AF that is at least partially rotational in nature (e.g., an area in which the duration of activation time is the greatest). Although the right atrium 210 is illustrated and described, rotors can exist within any chamber of the heart.

Figure 2B:
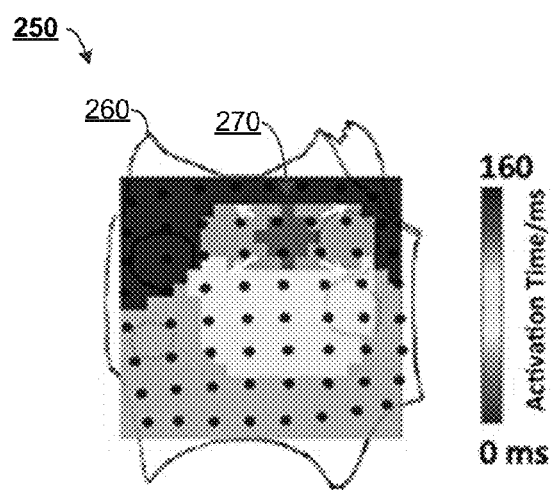
FIG. 2B depicts a map of activation time in a patient's left atrium, in accordance with some example implementations.

FIG. 2B depicts a fibrillatory source activation map 250 (in milliseconds according to the colored scale) in a patient's left atrium 260, in accordance with some example implementations. As illustrated, longer and/or more sustained activation of the left atrium 260 can emanate from a source 270. This source 270 can be regarded as a source of AF, and more particularly, a focal source. In some aspects, a focal source can be regarded as an organizing center from which AF is generated distally (e.g., an area from which the greatest duration of activation time emanates). Although the left atrium 270 is illustrated and described, focal sources can exist within any chamber of the heart.

Figure 2C:
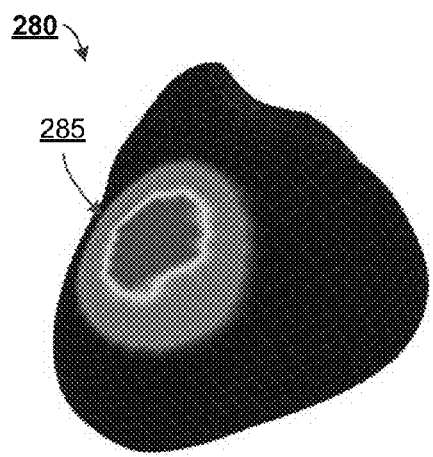
FIG. 2C depicts a fibrillatory source map for VF, in accordance with some example implementations.

FIG. 2C depicts a fibrillatory source map 280 for VF, in accordance with some example implementations. In some aspects, the fibrillatory source map 280 can be a product of the computer algorithms described herein. As illustrated, areas within the heart which maintain VF are color-coded according to the percent of VF cycles at which the VF source 285 is located at specific areas of the ventricle.

Figure 2D:
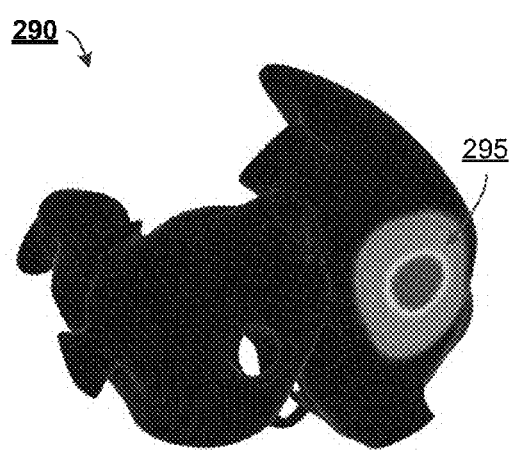
FIG. 2D depicts a fibrillatory source map for AF, in accordance with some example implementations.

FIG. 2D depicts a fibrillatory source map 290 for AF, in accordance with some example implementations. In some aspects, the fibrillatory source map 290 can be a product of the computer algorithms described herein. As illustrated, areas within the heart which maintain AF are color-coded according to the percent of AF cycles at which the AF source 295 is located at specific areas of the atrium.

Identification of the location of the source(s) 220, 270, 285, and 295 of VF/AF can be beneficial, as the knowledge of its location can help guide surgical procedures and minimize the amount of guesswork required by medical professionals. For example, in a patient with AF, individual rotors (e.g., as illustrated in FIG. 2A) or focal sources (e.g., as illustrated in FIG. 2B) can be targeted for ablation. Additionally, sources can be prioritized according to percentages of cycles/time emanating from such sources (e.g., as illustrated in FIGS. 2C and 2D). Ablation can then be delivered to areas which sustain the clinical arrhythmia rather than delivered to non-source tissue. In turn, the chances of the success of the procedure can be increase, as the location of the source(s) 220, 270 can be targeted specifically. Additionally, there can be a lower risk of damage to other organs, nerves, bones, muscles, etc. during surgery, decreased recovery time, and/or minimal scarring.

Heart failure is a complex disease that may involve and/or be based upon changes in ventricular shape, fiber orientation, ion channel expression remodeling, and/or other conditions/changes as well. Thus, computational models of the heart may be generated, modified, displayed, or otherwise utilized to identify a source/location of VF/AF based upon the conditions/changes of a specific patient according to the computing system 110 of FIG. 1, for example.

Computational models of the heart (or portions thereof) can be generated based upon imaging information (e.g., three-dimensional) representative of a heart and/or electrical data representative of an electrophysiology of the heart. At least some of the computational models may be patient-specific in the sense that the data used to generate the computational model and the parameters/metrics used in connection with the computational model may be specific to a given patient, taking conditions/changes into account. However, the time, effort, cost, and invasive procedures required to generate a patient-specific model can be prohibitive. For example, in order to measure electrical properties from within a heart, the positioning of an endocardial recording catheter or device may be required. Accordingly, at least some of the computational model may be general models in the sense that they are not representations of a specific patient's heart. These computational models can be generated manually, based upon patient-specific models or other patient-specific data, based upon measured/known characteristics of the human heart, and/or the like. Generated models can then be "transformed" to more specific patient configurations, as noted in the computing system 110 of FIG. 1, for example.

The general models can be modified to generate additional general models. For example, based upon a general model that has been verified as sufficiently accurate (e.g., through comparison to patient-specific models or other data obtained from a patient), the shape of the heart and/or location of the scars within the heart can be altered. As the shape and/or scarring of a heart can affect VF/AF, having additional models with varying hear shapes/scars can provide for additional accuracy in locating a source of VF/AF. In some implementations, thousands of computational models can be generated and/or stored within a model library 192. Any of these generation techniques can be manual, at least partially automated, and/or based on machine learning. In some aspects, the computational models can be regarded as finite element computational models of cardiac arrhythmia.

Measurements of a patient's cardiac electrical properties may be generated and/or received. For example, the computing system 100 may receive and/or record a patient's EKG data. In some implementations, the EKG data may be obtained from an EKG sensor device, such as 12-lead EKG, that records the continuous, dynamic signals of cardiac electrical function from multiple body locations (e.g., on the surface of the chest, arms, legs, head, etc.) of the patient. Additionally, the computing system 100 may receive and/or record a patient's endocardial data. In some implementations, the endocardial data can be obtained from a steerable mapping and/or ablation catheter located within at least one chamber of the heart (e.g. an ablation catheter located in the left and/or right ventricular for VF, or an ablation catheter within the left and/or right atria for atrial fibrillation), or from one or more basket-catheters, such as a 64-electrode basket catheter located within at least one chamber of the heart (e.g., one in the left ventricle and one in the right ventricle for VF, or one in the left atrium and on in the right atrium for AF), that records the continuous, dynamic signals of cardiac electrical function from within the heart of the patient.

In some aspects, the endocardial data can be matched (e.g., temporally) with EKG data, such that the computing system 100 has access to data representative cardiac electrical function from the interior and exterior of a patient's heart. Based upon the relationships between endocardial and EKG data, patterns can be identified and/or correlations can be defined in order to identify VF/AF sources (e.g., rotors or focal sources). In some implementations, endocardial and EKG data can be measured when a patient's heart is excited and/or when a patient's heart is in a relaxed state. In an example implementation, the heart's electrical activity can be recorded from routine pacing within the heart at one or more locations to establish the relationship between cardiac activation and surface EKG recordings and/or computed VCGs. In another implementation, VF/AF can be induced within a patient, and the electrical data during this time can be measured/recorded. As the data demonstrates how a patient's heart acts during VF/AF, it can be compared against baseline data and data from other patients to identify VF/AF sources.

Imaging data of a patient's heart (e.g., left atrium, right atrium, left ventricle, and/or right ventricle) may be received. For example, a computing system may receive and/or record image data that includes heart images (or portions thereof) obtained from a clinical cardiac CT scan device, 2D or 3D echocardiography devices, a myocardial perfusion scan device, an Mill device, a positron-emission-tomography device, an X-ray device, a fluoroscopy device, and/or other devices capable of generating or providing images of a heart (and/or portions thereof). To combine the 3D anatomic model of the heart with the endocardial and/or EKG data, the data processor may register (e.g., align) the data so that the endocardial and/or EKG data is aligned with the proper orientation(s) of the heart (e.g., of ventricle or atrial regions thereof).

A four-dimensional (4D) patient-specific computational model with data on a patient's electrical activity may be generated. For example, the computing system 110 may generate a 4D model based on 3D data received with the added dynamics from the electrical activity data. The 4D computational model may provide a 3D representation of the morphology and anatomy of the heart (or portions thereof) over time, and can provide time-varying electrical dynamics of the heart (or portions thereof), such as time-varying EKG and/or endocardial data. The electrical dynamics may include the activation patterns and/or the electrical trajectories of the activations through the myocardium. The electrical dynamics can include patterns (for example, sequences) of electrical repolarization/recovery. The model may also include additional/alternative aspects, such as the regional distribution of perfusion or infarction, which may be measured in individual patients or simulated.

In some implementations, a computational model may include EKG data overlaid and/or registered on 3D biventricular geometry of the patient's heart, the human fiber architecture of the heart, region(s) of heterogeneous conductivities caused by the presence of myocardial ischemia, infarction(s), anatomic (and/or functional) electrical conduction defects, such as partial and/or complete bundle branch block, and/or the like. The models can be generated using finite element meshes. Patient-specific finite element meshes of the heart (which may include its ventricular anatomy) may be generated from image data, such as clinical CT data, perfusion images, MRI data, and/or other types of image data.

The computational model may also include a heart's fiber architecture. The heart's fiber architecture may be estimated empirically using, for example, a log-Euclidean interpolation framework for registering DT-MR measurements to the anatomical models. Reconstructed diffusion tensors may be fitted as a field of log-transformed components in a corresponding anatomical mesh to interpolate local fiber, sheet, and sheet-normal axes. The fiber orientations in the resulting model may be mapped to a patient via large-deformation diffeomorphic mapping and reoriented based on the 3D deformation gradients between the template and target patient ventricular geometries to account for the effect of ventricular shape differences on fiber orientation. The resulting fiber-sheet model forms the local basis of transversely isotropic or orthotropic ventricular electrical conductivity (which may have a fiber-sheet anisotropy ratio of about 7:1 for example).

The computational model may also include regions of myocardial ischemia, infarction, and/or other like regions. When this is the case, myocardial ischemic or infarcted regions may be identified from, for example, perfusion images and/or sestamibi perfusion images obtained during stress and rest. The myocardial ischemia or infarction boundary regions may be demarcated on the generated anatomical meshes of the heart. For example, a patient may have a posteroseptal infarction, and may have an inferior infarction. These regions may be registered in the computational model as a binary field of normal and infarcted tissue.

The computational model may also include myocardial electrical conductance properties, such as electrical conductivity of the left ventricular and right ventricular endocardial or bulk myocardial tissue in the muscle fiber and transverse orientations as well as conductivities in the borderzone and/or infarcted or ischemic regions. The potentials may be described by a model of human ventricular myocytes modified to accommodate changes in channel kinetics occurring during heart failure. Action potential propagation may be modeled in a mono-domain or bi-domain reaction-diffusion mathematical framework. Electrical conductivity in the ventricular domain may be partitioned into left ventricle and right ventricle sub-endocardial regions (for example, ~3 mm transmurally adjacent to the ventricular cavities), infarct region, and the remaining bulk myocardium. The conductivity in the endocardial regions may be allowed to vary up to about for example 10 times that of bulk myocardium to account for the fast conduction of the Purkinje system, if not explicitly modeled. In infarcted or ischemic regions, conductivity may be isotropic, and the conductivity may be allowed to vary between about 10%-90% of that in the bulk myocardium.

Figure 3A:
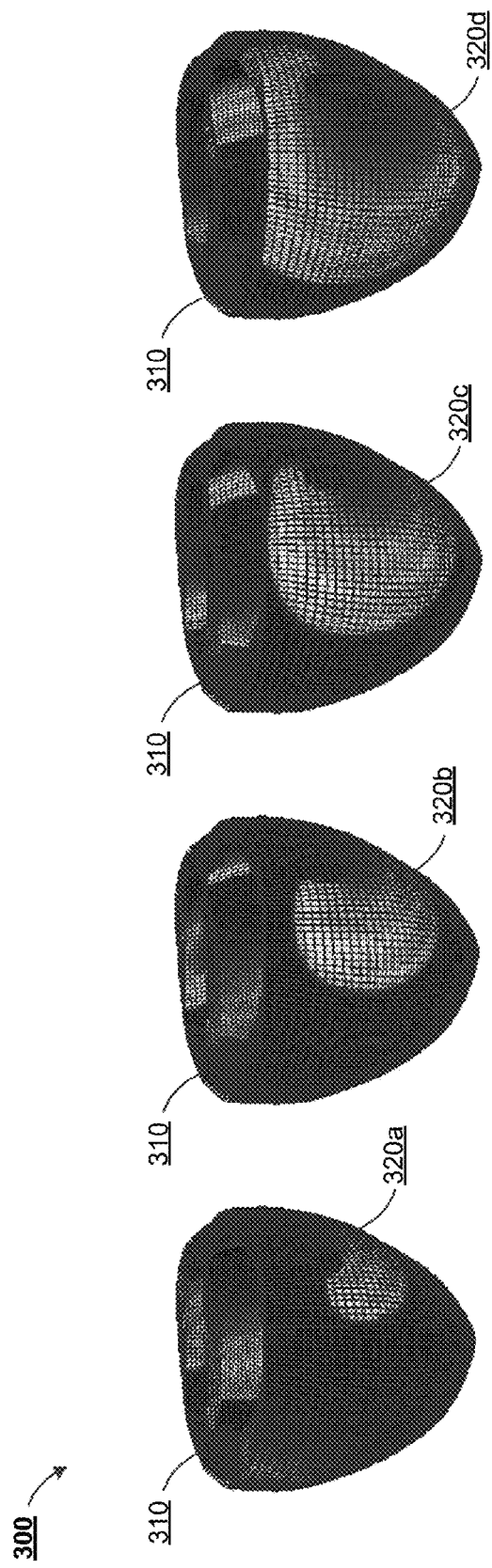
FIG. 3A depicts a biventricular computational model of an electrical rotor in the right ventricle, in accordance with some example implementations.

FIG. 3A depicts a biventricular computational model 300 of the left and right ventricles 310, in accordance with some example implementations. The computational model 300 is illustrated as a series of finite states of the left ventricle 310 with simulated myocardial voltage maps 320a-d (collectively referred to as a fibrillatory mapping 320) of myocardial voltage potentials in different locations. However, as described herein, the computational model 300 can be a three-dimensional model of the left and right ventricles 310 with the fibrillatory source mapping 320 (e.g., as a fourth dimension) moving around/across the surface of the left ventricle 310, in accordance with patterns indicative of VF. In some aspects, the fibrillatory source mapping 320 can be representative of endocardial, EKG, and/or VCG data.

Figure 3B:
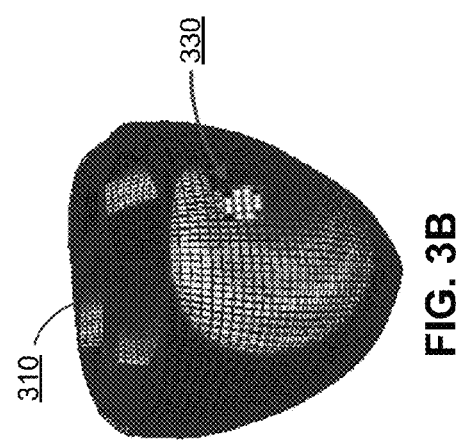
FIG. 3B depicts a biventricular computational model with an identified rotor, in accordance with some example implementations.

In some aspects, a source of VF can be identified based on the fibrillatory source mapping 320. For example, based upon the fibrillatory mapping 320, the computing system 110 can determine that electrical voltage indicative of VF rotates around a particular point/area of pro-arrhythmic substrate, which can be identified as a rotor in this case (e.g., alternatively as focal activation in others), as indicated by the highlighted source 330, illustrated through the white sites in FIG. 3B. In some aspects, the source 330 can be a location of diseased cardiac substrate.

In some implementations, the computational model 300 can be displayed via a user interface, and can include animations (e.g., showing movement of the fibrillatory mapping 320 and/or strength/percentage of VF/AF cycles/size of the source 330). In some aspects, the computational model 300 can be a 4D model and/or the fibrillatory source mapping 320 can be regarded as a fourth dimension. Although only four states of the left ventricle 310 and fibrillatory mapping 320 are illustrated, any number of states is possible (e.g., up to infinity). In some implementations, information about the source 330 (e.g., location, frequency/percentage of activation at particular locations, mechanism, etc.) can be stored and/or displayed to a user.

Different levels of granularity in the determined location of fibrillation sources are possible. For example, in some implementations, the fibrillation mechanism (e.g., rotors or focal sources), the specific chamber of the heart (e.g., left or right atrium or ventricle), and/or a region (e.g., anterior LV) of the fibrillation source can be identified. However, in some implementations, a specific location may be identified, which can be estimated based upon where an observed fibrillation source spends a certain amount of time or emanates from. The accuracy of identifying the location of a source of VF/AF can be based on the sensitivity of observed VCG patterns, the robustness of computational models from which a library of VCG patterns are generated, and/or the power of machine-learning methods.

Figure 4A:
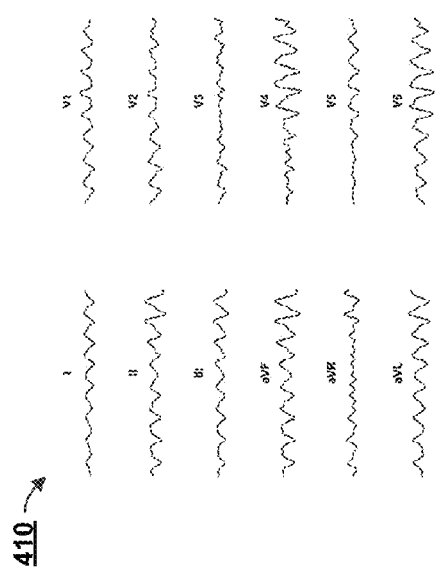
FIG. 4A depicts a graph of electrocardiogram (EKG) data computed from a computational model, in accordance with some example implementations.
Figure 4B:
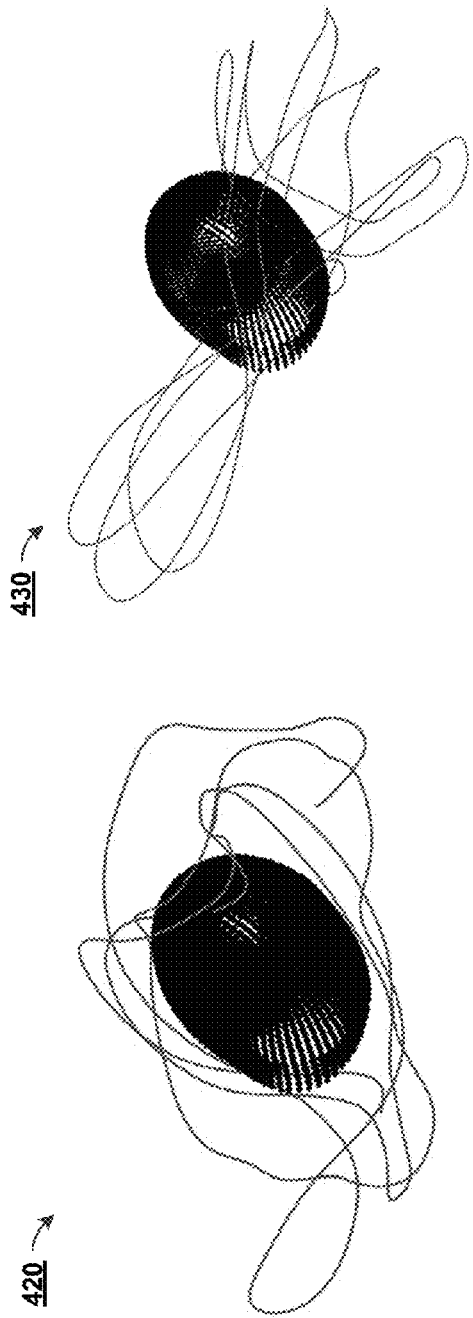
FIG. 4B depicts vectorcardiograms (VCG) computed from a computational model, in accordance with some example implementations.

As noted above, computational models can be based upon and/or include EKG data. FIG. 4A depicts a graph 410 of EKG data computed from a computational model, in accordance with some example implementations. In some aspects, this EKG data can be generated through the use of a 12-lead EKG sensor device. Although examples herein refer to endocardial and/or EKG data, the data may additionally or alternatively comprise other types of electrical data, such as VCG data. For example, FIG. 4B depicts a VCG 420 model with VCG tracings from a lateral viewpoint and a VCG model 430 with tracings from a superior viewpoint, in accordance with some example implementations. In some aspects, the black cardiac model located inside of the VCG tracings are just for perspective, and may not form part of the VCG tracings 420, 430. In some implementations, the VCG models 420, 430 can be generated based upon EKG data.

As noted above, the VCG models 420, 430 can be temporospatial VCG models constructed from a large number of realistic biventricular computational models of VF/AF (e.g., the computational models in the model library 192 and/or the patient-specific models 194). In some implementations, the model library 192 can include models simulating rotors/focal sources from different anatomical cardiac segments. More or less locations are possible, and in some aspects, the simulated locations can encompass the majority of potential source locations.

In some aspect, the coordinate axes of VCG data and/or the coordinate axes of the corresponding computational model can be rotated until they are correctly aligned with each other, as previously described with respect to the data transformation algorithms 197 of FIG. 1.

Figure 5A:
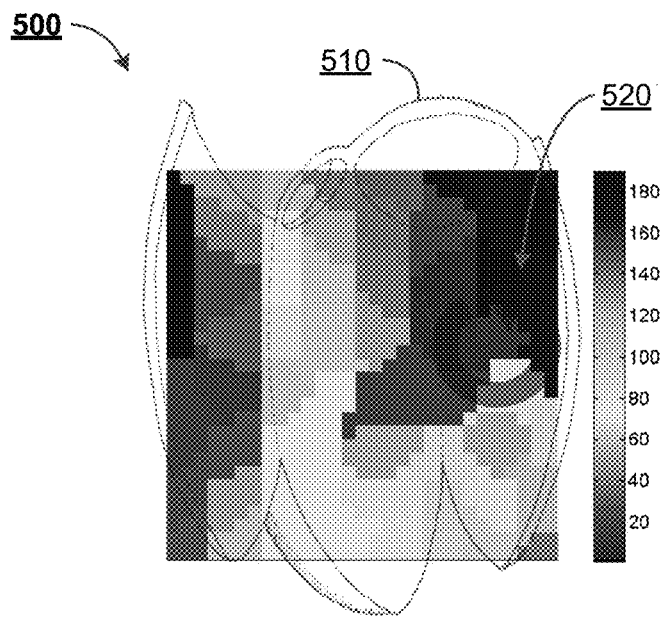
FIG. 5A depicts an endocardial, isochronal map of cardiac activation during VF in a patient's left ventricle, in accordance with some example implementations.
Figure 5B:
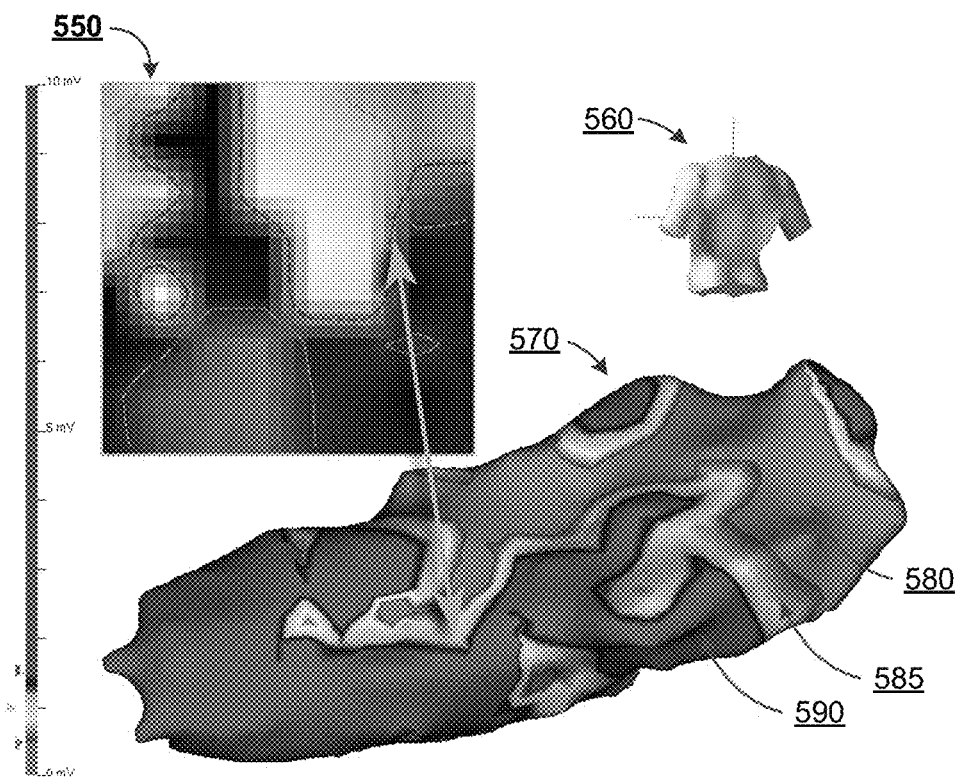
FIG. 5B depicts a VF source location within the patient's anatomy, according to endocardial voltage, in accordance with some example implementations.

FIG. 5A depicts a fibrillatory map 500 in a patient's left ventricle 510 during VF, in accordance with some example implementations. Similar to the fibrillatory source map 200 of FIG. 2A, the fibrillatory map 500 can be indicative of a VF rotor at a source 520. For example, FIG. 5B depicts a fibrillatory source map 550 of a rotor, in accordance with some example implementations. In some aspects, this map 550 can be a posterior view of a patient 560. As illustrated in the sectional view 570 of the fibrillatory source map 550, there may be areas of scar (gray) tissue 580, borderzone (red, orange, yellow, green, and blue) tissue 585, and/or normal (purple) tissue 590 in the patient's left ventricle. In some aspects, the myocardial scar/borderzone tissue 580, 585 can sustain VF, and therefore should be identified for ablation and/or external radiation therapy in order to reduce the future probability of arrhythmias for the patient 560. In some aspects, this scar tissue 580 and/or borderzone tissue 585 can be regarded as pro-arrhythmic cardiac substrate.

In order to identify the source of VF/AF within a patient, the computational models described herein can be compared against data obtained from the patient. In some aspects, the patient may know that they have VF/AF, but does not know the location of the source of their VF/AF. At this point, the patient may wish to learn the exact origin of their VF/AF (e.g., how bad is the patient's VF/AF and/or their risk of cardiac death), whether an implantable cardioverter-defibrillator (ICD) will be beneficial, whether ablation or surgery will be beneficial for preventing future arrhythmia, what the risks of surgery are, etc. Using the subject matter described herein, the patient may be able to go to a physician who takes non-invasive measurements of the patient, provides the measurement data to a computing apparatus, and receives data to better address the patient's questions and concerns.

Figure 6A:
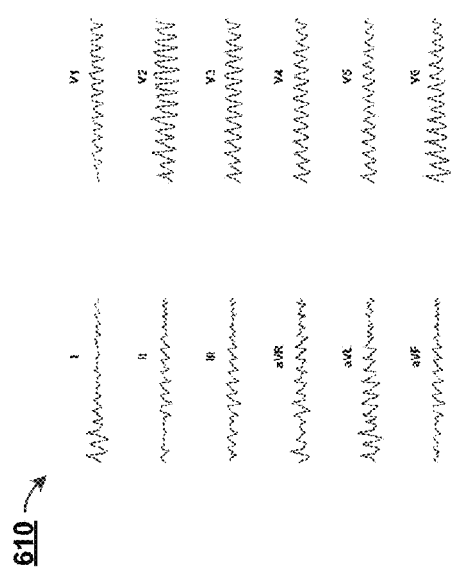
FIG. 6A depicts a graph of EKG readings during human VF, in accordance with some example implementations.
Figure 6B:
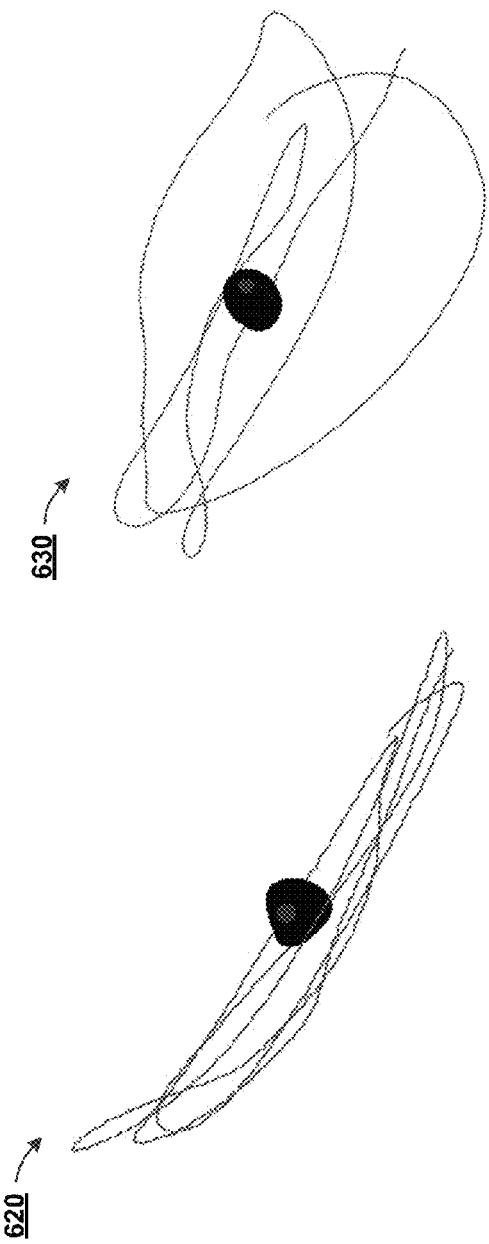
FIG. 6B depicts a VCG derived from recorded EKG data, in accordance with some example implementations.

In some implementations, the non-invasive measurements can include obtaining EKG data from the patient, such as through the use of a 12-lead EKG sensor. For example, FIG. 6A depicts a graph 610 of EKG readings during VF, in accordance with some example implementations. In some aspects, the EKG data is obtained during induced VF/AF. Based upon the EKG readings, VCG models and/or tracings can be generated for the patient. For example, FIG. 6B depicts a VCG model 620 from a lateral viewpoint and a VCG model 630 from a superior viewpoint, in accordance with some example implementations. In some aspects, the black cardiac model is just provided for orientation, and forms no part of the VCG models 620, 630 or the VCG tracings. In some implementations, the VCG models 620, 630 can be generated without the use of the EKG reading.

Once VCG models 620, 630 are obtained for the patient, they can be compared against VCG models stored in the VCG library 196, for example. Based upon the calculated similarities between the patient-derived VCG models 620, 630 and simulated/stored VCG models, VF/AF sources can be identified. In some aspects, the similarities can be measured in one or more (e.g., two) orthogonal planes. In some implementations, a Pearson correlation or similar comparison algorithm can be used to compare VCGs. Based upon the correlation factor, a VF/AF source can be identified within a patient.

As a patient may have more than one VF/AF source, multiple comparisons can be made. For example, a VCG can be obtained from a patient over a series of time intervals. In some aspects, a VCG can be generated for each time interval, which can be 1 ms in duration, for each VF cycle (which can be approximately 200 ms in duration). Each of the VF cycle VCG can be compared against stored VF cycle VCGs to identify which VCG correlates most with the patient's. A corresponding computational model from the model library 192 can be identified based on whichever VCG has the highest correlation. The data associated with the identified computational model, including but not limited to VF source type, location, direction of rotation (if any), and/or the like as described herein, can be regarded as representative of the patient's heart during the specific time interval. Based upon at least a portion of the identified computational models, an estimated computational model can be generated for the patient. In some implementations, a subset of computational models of interest from the model library 192 can be identified based upon the shape of the patient's heart, location of scar, conduction properties, and/or the like (e.g., as determined by CT, MRI, echo, X-ray, fluoroscopy, or other imaging data). The identified set of computational models can be correlated with VCGs from the VCG library 196, which can be the VCGs selected for comparison with the patient.

Different rotor locations can create significantly different VCG loops. Therefore, the generation and comparison of patient-derived VCGs against known/estimated patterns for VF/AF sources can be an accurate method for identifying VF/AF sources in patients.

In some implementations, a fibrillatory source map, such as the fibrillatory source map 280 of FIG. 2C and/or the fibrillatory source map 290 of FIG. 2D, for illustrating the location of the VF/AF source can be generated. For example, based upon comparing the VCGs, a determination may be made as to how long a VF/AF source spends in one or more locations. This temporal/percentage information can be used to generate a fibrillatory source map, and/or the map can be overlaid on heart imaging data. Displaying the heart imaging data (e.g., a 3D model) with the fibrillatory source map can allow a medical professional to identify additional characteristics about the VF/AF source(s), and/or to target the source location for radiofrequency, cryogenic, ultrasound, or laser ablation, external beam radiation, revascularization, gene transfer therapy, or other intervention to reduce future arrhythmia burden.

In some implementations, additional computational models can be generated based upon the comparison of patient-derived VCGs to stored VCGs. For example, one or more models can be identified from the model library 192 that is most similar to the VF/AF source(s) identified within the patient. These one or more models can be combined to generate a composite model, which can include data representative of all VF/AF sources in the patient. Using the composite model, one VF/AF source can be removed (e.g., removal is simulated) to generate a new model, which can be compared against the composite model to determine whether the removal of each VF/AF source would be beneficial to the patient. If the change in VF/AF exhibited between the composite model and the new model is below a threshold value/percentage, then it can be determined that the removal of the VF/AF source may not be beneficial to the patient. The threshold value/percentage can vary depending upon the patient, medical professional, and/or other factors.

Although the measurements/comparisons described above are for a patient's left ventricle, measurements/comparisons can be performed in a similar fashion, but with respect to a patient's right ventricle. For example, FIG. 7A depicts a computational model 700 of a right ventricle 710, in accordance with some example implementations. As illustrated, the computational model 700 can include a plurality of myocardial voltage maps 710*a-d*, illustrated as a series of finite states, which may form a mapping of cardiac electrical activation in the right ventricle 710.

The computational model 700 can be based upon EKG data and/or can be used to generate EKG data. For example, FIG. 7B depicts a graph 730 of EKG readings generated from the computational model, in accordance with some example implementations. The process to create EKG readings can be through first computing VCGs from the electrical dipole of a computational model for each time period. EKG tracings can then be computed. For example, FIG. 7C depicts VCG models 740, 750, generated from a cardiac model, in accordance with some example implementations. One or more VCG models, such as the VCG model 740 from a lateral viewpoint and/or the VCG model 750 from a vertical viewpoint are computed from the computational model. EKG tracings may be derived from this data thereafter. Importantly, the VCG models 740, 750, allow comparison and matching to VCG data from a patient, as described herein. As illustrated, the VCGs models 740, 750 are color-coded based on timing information.

Figure 8A:
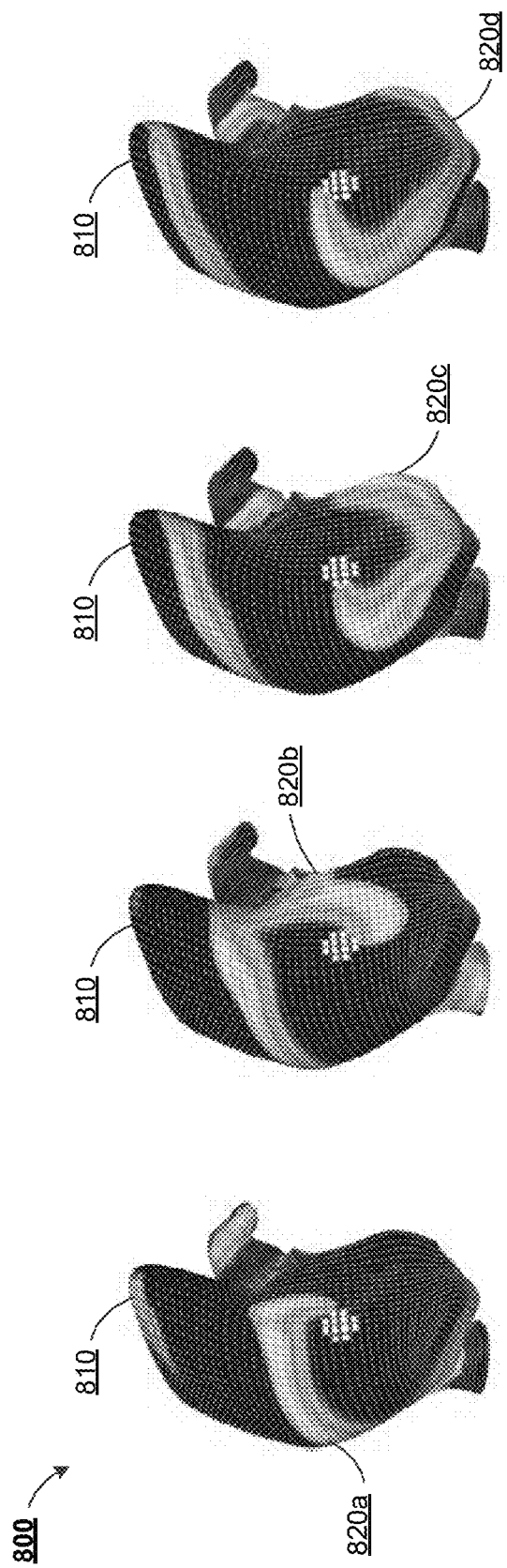
FIG. 8A depicts a computational model of the right and left atria, in accordance with some example implementations.
Figure 8B:
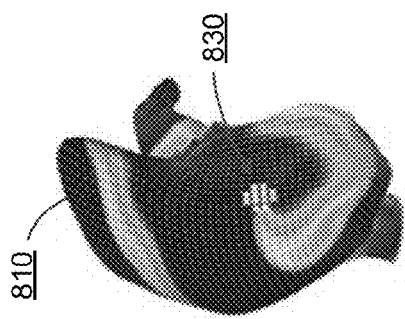
FIG. 8B depicts a computational model of the right and left atria with a simulated diseased substrate which maintains an identified rotor, in accordance with some example implementations.

Although the measurements/comparisons described above are for a patient's left and right ventricles in VF, measurements/comparisons can be performed in a similar fashion, but with respect to a patient's right or left atria during AF. For example, FIG. 8A depicts a computational model 800 of the left and right atria 810, in accordance with some example implementations. As illustrated, the computational model 800 can include myocardial voltage maps 820*a-d*, which can be representative of and/or based on endocardial and/or EKG data. From the computational model 800, the location of a source of AF can be identified (white dots). For example, FIG. 8B depicts the computational model 800 of the right atrium 810 with an identified rotor substrate 830 (denoted by white dots), in accordance with some example implementations.

Figure 9:
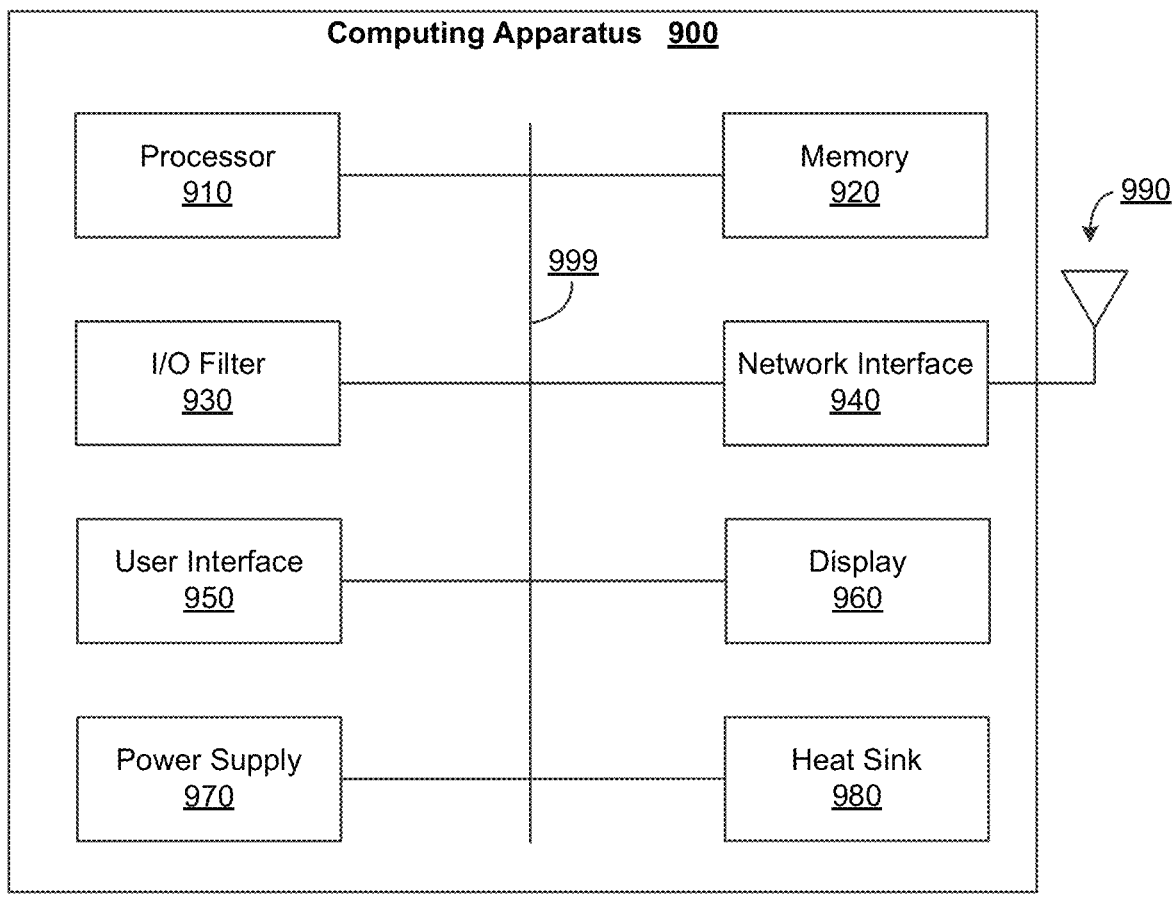
FIG. 9 depicts a block diagram of an example computing apparatus, in accordance with some example implementations.

FIG. 9 illustrates an example computing apparatus 900 which may be used to implement one or more of the described devices and/or components, in accordance with some example implementations. For example, at least a portion of the computing apparatus 900 may be used to implement at least a portion of the computing device 110, an apparatus providing the database 120, an apparatus providing the external software 130, one or more of the user access devices 140, one or more of the sensor devices 150, and/or the access device 165. Computing apparatus 900 may perform one or more of the processes described herein.

As illustrated, computing apparatus 900 may include one or more processors such as processor 910 to execute instructions that may implement operations consistent with those described herein. Apparatus 900 may include memory 920 to store executable instructions and/or information. Memory 920 may include solid-state memory, solid-state disk drives, magnetic disk drives, or any other information storage device. In some aspects, the memory 920 may provide storage for at least a portion of a database (e.g., the database 120 or some other organization of data). Apparatus 900 may include a network interface 940 to a wired network or a wireless network, such as the network 160 of FIG. 1. Wireless networks may include WiFi, WiMax, and cellular networks (2G/3G/4G/5G), and/or any other wireless network. In order to effectuate wireless communications, the network interface 940, for example, may utilize one or more antennas, such as antenna 980.

Apparatus 900 may include one or more user interface, such as user interface 950. The user interface 950 can include hardware or software interfaces, such as a keyboard, mouse, or other interface, some of which may include a touchscreen integrated with a display 930. The display 930 may be used to display information such as promotional offers or current inventory, provide prompts to a user, receive user input, and/or the like. In various implementations, the user interface 950 can include one or more peripheral devices and/or the user interface 950 may be configured to communicate with these peripheral devices.

In some aspects, the user interface 950 may include one or more of the sensors described herein and/or may include an interface to one or more of the sensors described herein. The operation of these sensors may be controlled at least in part by a sensor module 960. The apparatus 900 may also comprise and input and output filter 970, which can filter information received from the sensors or other user interfaces, received and/or transmitted by the network interface, and/or the like. For example, signals detected through sensors can be passed through the filter 970 for proper signal conditioning, and the filtered data may then be passed to the microcontroller sensor module 960 and/or processor 910 for validation and processing (e.g., before transmitting results or an indication via the network interface 940). The apparatus 900 may be powered through the use of one or more power sources, such as power source 990. As illustrated, one or more of the components of the apparatus 900 may communicate and/or receive power through a system bus 999. In some aspects, the apparatus 900 may be regarded as at least a portion of a server or an apparatus which utilizes at least a portion of a server.

Figure 10:
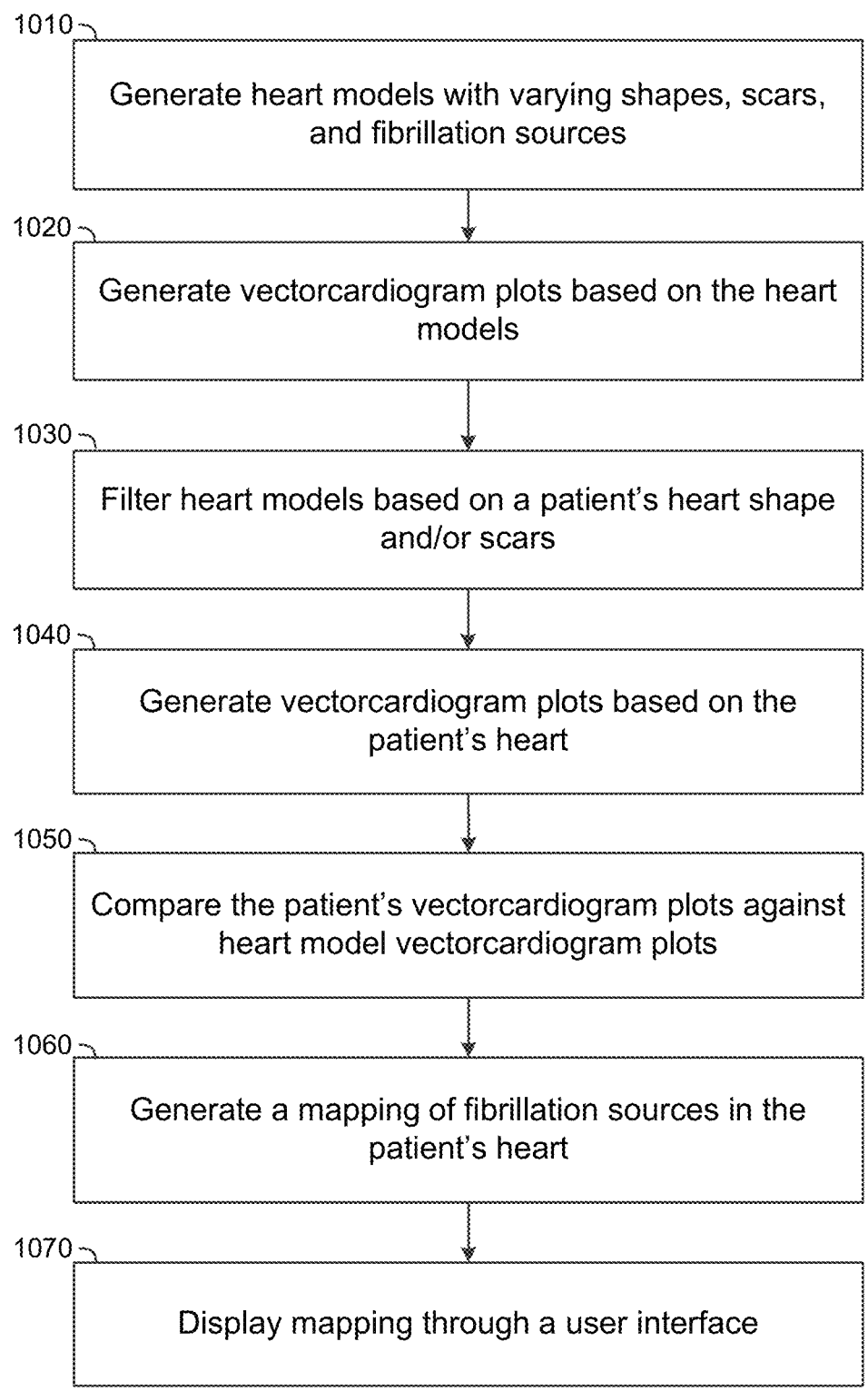
FIG. 10 depicts an example of a method for computational localization of fibrillation sources, in accordance with some example implementations.

FIG. 10 illustrates a flowchart of a method for computational localization of fibrillation sources, in accordance with some example implementations. In various implementations, the method 1000 (or at least a portion thereof) may be performed by one or more of the computing device 110, an apparatus providing the database 120, an apparatus providing the external software 130, one or more of the user access devices 140, one or more of the sensor devices 150, the access device 165, the computing apparatus 900, other related apparatuses, and/or some portion thereof.

Method 1000 can start at operational block 1010 where the apparatus 900, for example, can generate heart models with varying shapes, scars, and fibrillation sources. Other aspects can additionally or alternatively be used, such as geometries, fiber orientations, fibrillation source types, fibrillation source locations, and/or the like.

Method 1000 can proceed to operational block 1020 where the apparatus 900, for example, can generate vectorcardiogram plots based on the heart models. For example, the heart models can be used to compute model VCGs and/or generate a comprehensive VCG library.

Method 1000 can proceed to operational block 1030 where the apparatus 900, for example, can filter heart models based on a patient's heart shape and/or scars. In some aspects, the filtering can be based on computerized tomography imaging data, magnetic resonance imaging data, echocardiography data, X-ray data, fluoroscopy data, and/or the like.

Method 1000 can proceed to operational block 1040 where the apparatus 900, for example, can generate vectorcardiogram plots based on the patient's heart.

Method 1000 can proceed to operational block 1050 where the apparatus 900, for example, can compare patient's vectorcardiogram plots against heart model vectorcardiogram plots. The vectorcardiogram plots can be retrieved, such as from a VCG library. In some implementations, a subset of the vectorcardiogram plots in a VCG library can be selected based upon the filtered heart models. The comparison can comprise determining, for each of the stored VCGs, a correlation factor between a generated VCG and the stored VCGs, and at least one matched VCG can be identified as the stored VCG(s) with a highest correlation factor.

Method 1000 can proceed to operational block 1060 where the apparatus 900, for example, can generate a mapping of fibrillation sources in the patient's heart. In some implementations, a computational model can include a three-dimensional mesh in a heart shape and a finite state fibrillatory source map of cardiac electrical activations mapped to the mesh. In some implementations, method 1000 can involve generating electrocardiogram plots based on the patient's heart, and/or generating the representation of electrical activation of the patient's heart based on the electrocardiogram plots.

Method 1000 can proceed to operational block 1070 where the apparatus 900, for example, can display mapping through a user interface (e.g., user interface 950). The mapping can be displayed through the use of heart models, which can include one or more of the left atrium, the right atrium, the ventricle, or the right ventricle. The models can be two-dimensional, three-dimensional, four-dimensional, and/or may be animated. In some aspects, displaying can enable guiding of an ablation procedure using radiofrequency, cryogenics, ultrasound, laser, external beam radiation, and/or the like.

In some implementations, method 1000 can involve generating a plurality of vectorcardiogram plots based on one or more stored computational models, and/or generating one or more electrocardiogram plots based on the plurality of vectorcardiogram plots.

Performance of the method 1000 and/or a portion thereof can allow for identification of VF/AF sources with increased accuracy, decreased invasiveness, and/or decreased cost.

Figure 11:
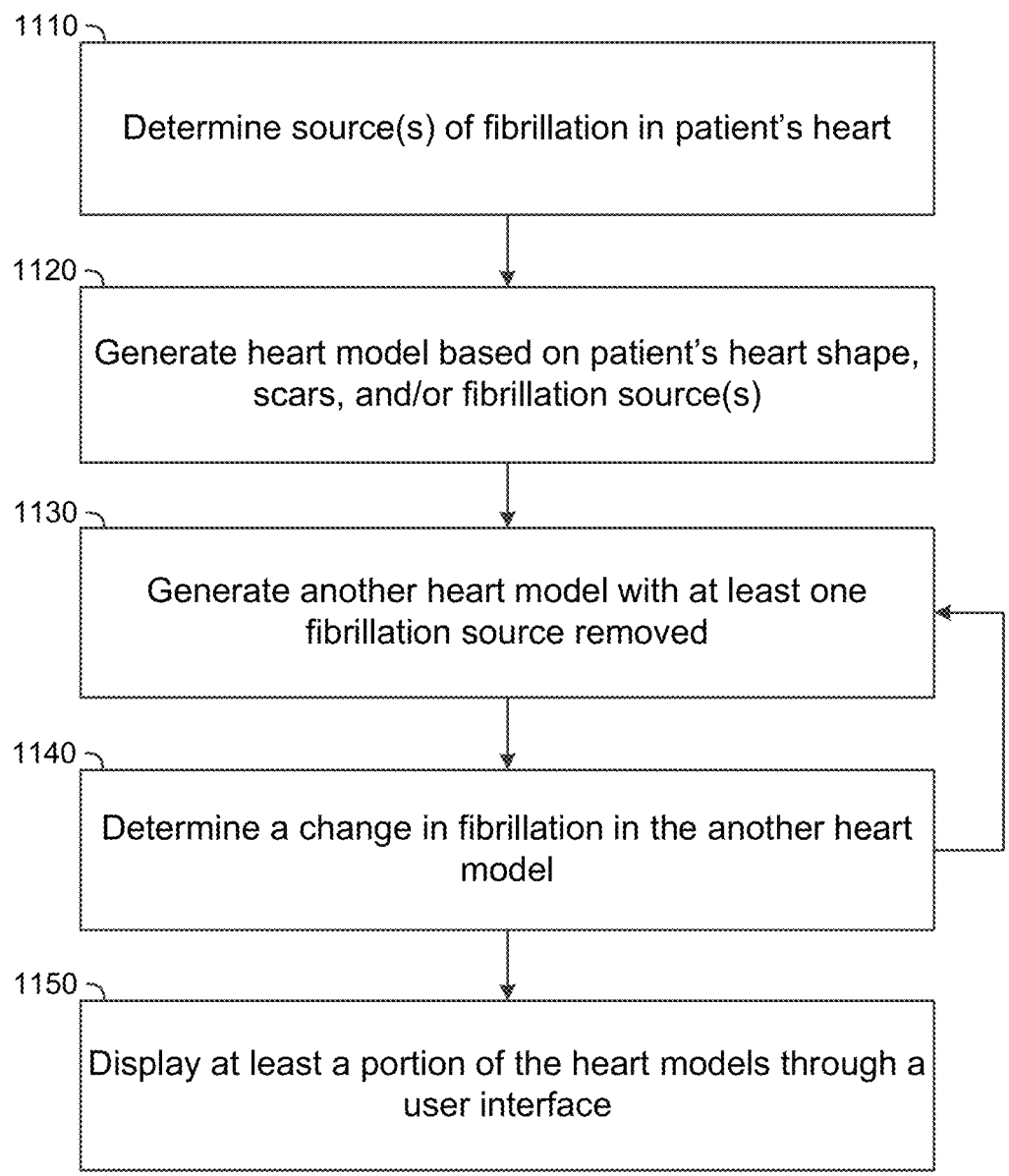
FIG. 11 depicts an example of a method for computing the effect of ablation and a subsequent risk of cardiac fibrillation, in accordance with some example implementations.

FIG. 11 illustrates a flowchart of a method for computational localization of fibrillation sources, in accordance with some example implementations (e.g., similar to the illustrations in FIG. 12). In various implementations, the method 1000 (or at least a portion thereof) may be performed by one or more of the computing device 110, an apparatus providing the database 120, an apparatus providing the external software 130, one or more of the user access devices 140, one or more of the sensor devices 150, the access device 165, the computing apparatus 900, other related apparatuses, and/or some portion thereof.

Method 1100 can start at operational block 1110 where the apparatus 900, for example, can determine source(s) of fibrillation in patient's heart. In some implementations, the identification of fibrillation sources can be similar to identification procedures discussed with respect to the method 1000 of FIG. 10.

Method 1100 can proceed to operational block 1120 where the apparatus 900, for example, can generate heart model based on patient's heart shape, scars, and/or fibrillation source(s).

Method 1100 can proceed to operational block 1130 where the apparatus 900, for example, can generate another heart model with at least one fibrillation source removed. In some aspects, a computational model can be generated by removing one of the one or more fibrillation sources from an original computational model Method 1100 can proceed to operational block 1140 where the apparatus 900, for example, can determine a change in fibrillation in the another heart model.

Method 1100 can return to operational block 1130 if there are additional sources to evaluate. For example, if three sources of VF/AF were identified, then the method 1100 can evaluate the removal of each of the sources, alone or in combination with any number of the other two sources (e.g., seven unique evaluations). Through this procedure, a user (e.g., medical professional) can identify a best course of action in removing VF/AF sources.

Method 1100 can proceed to operational block 1150 where the apparatus 900, for example, can display at least a portion of the heart models through a user interface (e.g., user interface 950). The heart models can include one or more of the left atrium, the right atrium, the ventricle, or the right ventricle. The models can be two-dimensional, three-dimensional, four-dimensional, and/or may be animated. In some aspects, a side-by-side comparison of models with and without VF/AF sources can be provided. In some aspects, method 1100 can include determining a change in fibrillation between the new computational model(s) and the original computational model(s). In some aspects, the displaying the side-by-side comparison can enables a targeted ventricular fibrillation or ventricular fibrillation ablation therapy by providing predictive ablation outcome data and/or selection of an optimized ablation strategy.

Performance of the method 1100 and/or a portion thereof can allow for determinations of whether the elimination of each individual VF/AF source may or may not benefit a patient. For example, if the change in VF/AF in a model where a particular source is removed is not decreased by a threshold amount (e.g., percentage), then invasive procedures removing (or reducing the strength of) the particular source can be avoided.

Although several aspects are described herein with respect to VF and AF, other implementations are possible. For example, other arrhythmia or patterns within humans and/or animals can be observed and/or a source thereof can be identified. If a source of an abnormal pattern within a patient is identified, then it may displayed (e.g., in two-dimensional or three-dimensional modelling) to a user (e.g., a medical professional) such that the user can see inside of a patient's body without making an incision.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic input, speech input, tactile input, and/or the like. Other possible input devices include touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such phrases are intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." The use of the term "based on," above and in the claims is intended to mean "based at least in part on," such that a feature or element that is not recited is also permissible.

The illustrated methods are exemplary only. Although the methods are illustrated as having a specific operational flow, two or more operations may be combined into a single operation, a single operation may be performed in two or more separate operations, one or more of the illustrated operations may not be present in various implementations, and/or additional operations which are not illustrated may be part of the methods. In addition, the logic flows depicted in the accompanying figures and/or described herein do not necessarily require the particular order shown, or sequential order, to achieve desirable results. Other implementations may be within the scope of the following claims.

What is claimed is:

1. A method performed by one or more computing systems, the method comprising:

accessing a library including a plurality of computational models, each of the plurality of computational models associated with a set of electrical activations of a heart mapped to a three-dimensional finite element cardiac mesh, each of the plurality of computational models further being associated with a set of characteristics of the heart including a source location of a source of an arrhythmia, at least two sets of electrical activations being associated with different source locations;

generating, based at least on a first set of electrical activations associated with a first computational model from the library, a first simulated cardiogram, the first simulated cardiogram being associated with a first source location of the first computational model;

generating, based at least on a second set of electrical activations associated with a second computational model from the library, a second simulated cardiogram associated with a second source location of the second computational model, the second computational model being associated with a different heart shape and/or a different scar location when compared to the first computational model;

training, based at least on the first simulated cardiogram and the second simulated cardiogram, a machine-learning algorithm, the trained machine-learning algorithm configured to receive an input including a patient cardiogram collected from a patient and generate an output including a patient source location of a patient source of an arrhythmia associated with the patient cardiogram; and determining, based at least on the output of the trained machine-learning algorithm, a treatment of the patient, the treatment including an ablation, and the patient source location output by the machine-learning algorithm being a target source location for the ablation.

2. The method of claim 1 further comprising:
generating, based on a plurality of sets of characteristics of a heart including two or more different source locations for an arrhythmia, the plurality of computational models; and
storing, in the library, the plurality of computational models.

3. The method of claim 1, wherein the machine-learning algorithm is further trained based on a non-simulated cardiogram generated based on a patient-specific model associated with a set of patient-specific characteristics.

4. The method of claim 1 wherein the plurality of computational models are associated with non-patient specific characteristics.

5. The method of claim 1, further comprising applying the trained machine-learning algorithm to the patient cardiogram in order to identify, as the target source location for the ablation, the patient source location of the patient source of the arrhythmia.

6. The method of claim 1, wherein the first simulated cardiogram and/or the second simulated cardiogram comprise an electrocardiogram.

7. The method of claim 1, wherein the first simulated and/or the second simulated cardiogram comprise a vectorcardiogram.

8. The method of claim 1, wherein the plurality of computational models are associated with a specific source of arrhythmia including rotors or focal sources.

9. The method of claim 1 wherein the machine-learning algorithm is trained to identify one or more source locations of a specific source of arrhythmia including rotors or focal sources.

10. One or more computing systems comprising:
one or more processors; and
one or more memories storing instructions, which when executed by the one or more processors, cause operations comprising:
accessing a plurality of computational models derived from electrical activations of a heart, each the plurality of computational models associated with a characteristic of a pattern of electrical activity of the heart that is a source location of a source of the pattern of electrical activity of the heart, the electrical activations being mapped to a three-dimensional finite element mesh representing the heart, at least two electrical activations being associated with different source locations;
generating, based at least on a first electrical activations associated with a first computational model, a first simulated representation of the electrical activations of the heart;
generating, based at least on a second electrical activations associated with a second computational model, a second simulated representation of the electrical activations of the heart, the second computational model being associated with a different heart shape and/or a different scar location when compared to the first computational model;
training, based at least on the first simulated representation and the second simulated representation, a machine-learning algorithm, the trained machine-learning algorithm configured receive an input including a patient representation of electrical activations of the heart of a patient and generate an output identifying a patient source location of a patient source of the pattern of electrical activity of the heart of the patient; and
determining, based the output of the machine-learning algorithm, a treatment of the patient.

11. The one or more computing systems of claim 10, wherein the instructions further cause operations comprising:
generating, based on each of a plurality of sets of characteristics of the heart, a corresponding one of a plurality of computational models of electrical activations of the heart.

12. The one or more computing systems of claim 11, wherein each of the plurality of computational models is associated with a source type of the source.

13. The one or more computing systems of claim 10, wherein the first simulated representation of electrical activations, the second simulated representation of electrical activations, and the patient representation of electrical activations are cardiograms.

14. The one or more computing systems of claim 10, wherein the first simulated representation and the second simulated representation are each associated with a characteristic that is a source type of the pattern of electrical activity of the heart.

15. The one or more computing systems of claim 10, wherein the pattern of electrical activity is an arrhythmia, and wherein the machine-learning algorithm is trained to identify one or more source locations of a specific source of patterns of electrical activity including rotors or focal sources.

16. A method performed by one or more computing systems for identifying a source location of a source of an arrhythmia of a patient, the method comprising:
collecting a patient cardiogram of the patient;
applying, to the patient cardiogram, a machine-learning algorithm to identify the source location of the source of the arrhythmia for the patient, the machine-learning algorithm trained based on a plurality of training cardiograms, the plurality of training cardiograms including a first simulated cardiogram and a second simulated cardiogram, the first simulated cardiogram generated based on a first computational model, the second simulated cardiogram generated based on a second computational model, each of the first computational model and the second computational model being associated with a set of characteristics of a heart including one or more source locations of various sources of an arrhythmia, the second computational model being associated with a different heart shape and/or a different scar location when compared to the first computational model, and each of the first computation model and the second computation model further being associated with a set of electrical activations of a heart mapped to a three-dimensional finite element cardiac mesh; and
determining, based at least on an output of the machine-learning algorithm identifying the source location of the source of the arrhythmia for the patient, a treatment of the patient.

17. The method of claim 16, wherein the plurality of the training cardiograms further includes a non-simulated cardiogram that is generated based on a patient-specific model associated with a set of patient-specific characteristics.

18. The method of claim 16, wherein the machine-learning algorithm is trained to identify one or more source locations of a specific source of arrhythmia including rotors or focal sources.

19. The method of claim 16 wherein the machine-learning algorithm is stored in a cloud-based system and the patient cardiogram is provided via a gateway to the cloud-based system to identify the source location of the source of the arrhythmia for the patient.

20. The method of claim 16 further comprising outputting an indication of the identified source location to guide an ablation procedure on the heart of the patient.

21. One or more computing systems comprising:
one or more processors; and
one or more memories storing instructions, which when executed by the one or more processors, cause operations comprising:
collecting a patient representation of electrical activations of a heart of a patient;
applying, to the patient representation of electrical activations, a machine-learning algorithm to identify a characteristic of a pattern of electrical activity of the heart of the patient, the characteristic being a source location of a pattern of electrical activity of the heart, the machine-learning algorithm trained based on a plurality of training representations of electrical activations, the plurality of training representations of electrical activations including a first simulated representation of electrical activations and a second simulated representation of electrical activations, each of the first simulated representation and the second simulated representation being associated with a corresponding source location of the pattern of electrical activity, each of the one or more simulated representations of electrical activations generated based on a computational model including electrical activations mapped to a three-dimensional finite element mesh representing the heart, the first simulated representation and the second simulated representation being generated based on computational models associated with different heart shapes and/or different scar locations; and
determining, based at least on an output of the machine-learning algorithm identifying the source location of the pattern of electrical activity of the heart of the patient, a treatment of the patient.

22. The one or more computing systems of claim 21, wherein the plurality of training representations of electrical activations further includes a non-simulated representation of electrical activations that is generated based on a patient-specific model associated with a set of patient-specific characteristics.

23. The one more computing systems of claim 21, wherein the plurality of training representations of electrical activations and the patient representation of electrical activations are cardiograms.

24. The one or more computing systems of claim 21, wherein the pattern of electrical activity is an arrhythmia, and wherein the machine-learning algorithm is trained to identify one or more source locations of a specific source of arrhythmia including rotors or focal sources.

25. The one or more computing systems of claim 21, wherein the machine-learning algorithm is stored in a cloud-based system and the patient representation of electrical activations is provided via a gateway to the cloud-based system to identify a source location of a source of the pattern of electrical activity of the heart of the patient.

26. The one or more computing systems of claim 25, wherein the instructions further cause operations to output an indication of the identified source location to guide an ablation procedure on the heart of the patient.

27. The method of claim 1, wherein the machine-learning algorithm is trained using cycles derived from the cardiograms and wherein the cycles derived from a cardiogram are associated with the source location that is associated with a corresponding cardiogram from which the cycles are derived.

28. One or more computing systems comprising:
one or more processors; and
one or more memories storing instructions, which when executed by the one or more processors, cause operations comprising:
collecting a patient representation of electrical activations of a heart of a patient;
applying, to the patient representation of electrical activations, a machine-learning algorithm to identify a characteristic of a pattern of electrical activity of the heart of the patient, the characteristic being a source location of a pattern of electrical activity of the heart, the machine-learning algorithm trained based on a plurality of training representations of electrical activations, the plurality of training representations of electrical activations including a first simulated representation of electrical activations and a second simulated representation of electrical activations, each of the first simulated representation and the second simulated representation being associated with a corresponding source location of the pattern of electrical activity, each of the one or more simulated representations of electrical activations generated based on a computational model including electrical activations mapped to a three-dimensional finite element mesh representing the heart, the first simulated representation and the second simulated representation being generated based on computational models associated with different heart shapes and/or different scar locations;
determining, based at least on an output of the machine-learning algorithm identifying the source location of the pattern of electrical activity of the heart of the patient, a treatment of the patient; and
displaying a graphic representing a three-dimensional representation of a heart, the graphic including an indication of the identified source location.

29. The one or more computing systems of claim 28, wherein the operations further comprise displaying via a user interface an animation showing movement of a source mapping of a computational model.

* * * * *